United States Patent [19]

Mihara et al.

[11] Patent Number: 6,010,851
[45] Date of Patent: Jan. 4, 2000

[54] METHOD FOR PRODUCING NUCLEOSIDE-5'-PHOSPHATE ESTER

[75] Inventors: Yasuhiro Mihara; Takashi Utagawa, both of Kawasaki; Hideaki Yamada, Kyoto; Yasuhisa Asano, Imizu-gun, all of Japan

[73] Assignee: Ajinomoto Co., Inc., Tokyo, Japan

[21] Appl. No.: 08/750,145

[22] PCT Filed: May 24, 1996

[86] PCT No.: PCT/JP96/01402

§ 371 Date: Jan. 21, 1997

§ 102(e) Date: Jan. 21, 1997

[87] PCT Pub. No.: WO96/37603

PCT Pub. Date: Nov. 28, 1996

[30] Foreign Application Priority Data

May 25, 1995 [JP] Japan ..................................... 7-149781
Mar. 26, 1996 [JP] Japan ..................................... 8-094680

[51] Int. Cl.[7] ...................................................... C12Q 1/68
[52] U.S. Cl. ................................................. 435/6; 536/26.6
[58] Field of Search .............................. 536/26.6; 435/21, 435/196

[56] References Cited

FOREIGN PATENT DOCUMENTS

| 39-29858 | 12/1964 | Japan . |
|---|---|---|
| 42-1186 | 1/1967 | Japan . |
| 53-56390 | 5/1978 | Japan . |
| 56-82098 | 7/1981 | Japan . |
| 63-230094 | 9/1988 | Japan . |
| 07 231793 | 9/1995 | Japan . |

OTHER PUBLICATIONS

Abstract for Congress of the Society for Fermentation and Bioengineering, p. 356, Oct. 10, 1994, Y. Asano, et al., "Phosphorylation of Nucleosides With Pyrophosphate As A Phosphate Donor" (with English Translation).

Nippon Nogeikagaku Kaishi, vol. 69, p. 270 (20a10), Jul. 5, 1995, Y. Mihara, et al., "Enzymatic Phosphorylation Reaction Of Nucleoside Using Pyrophosphate As A Phosphate Donor" (With English Translation).

Efstratiadis et al., Nucleic Acids Research, 4(12):4165–74, Abstract, Dec. 1977.

*Primary Examiner*—Scott W. Houtteman
*Attorney, Agent, or Firm*—Oblon, Spivak, McClelland, Maier & Neustadt, P.C.

[57] ABSTRACT

Nucleoside-5'-phosphate ester is produced inexpensively and efficiently by allowing an acid phosphatase, especially an acid phosphatase having a lowered phosphomonoesterase activity to act under a condition of pH 3.0 to 5.5 on a nucleoside and a phosphate group donor selected from the group consisting of polyphosphoric acid or a salt thereof, phenylphosphoric acid or a salt thereof, and carbamyl phosphate or a salt thereof to produce nucleoside-5'-phosphate ester, and collecting it.

31 Claims, 11 Drawing Sheets

SB: Sau3AI / BamHI junction  B: Bam HI  E: EcoRI  K: KpnI
H: HindIII  N: NcoI  P: PstI F I G. 6
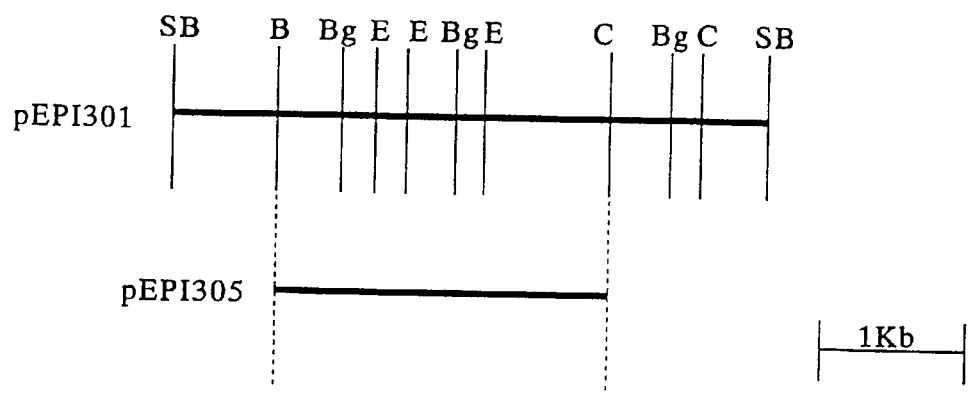
SB: Sau3AI / BamHI junction  B: BamHI  Bg: BglII  C: ClaI  E: EcoRI F I G. 7
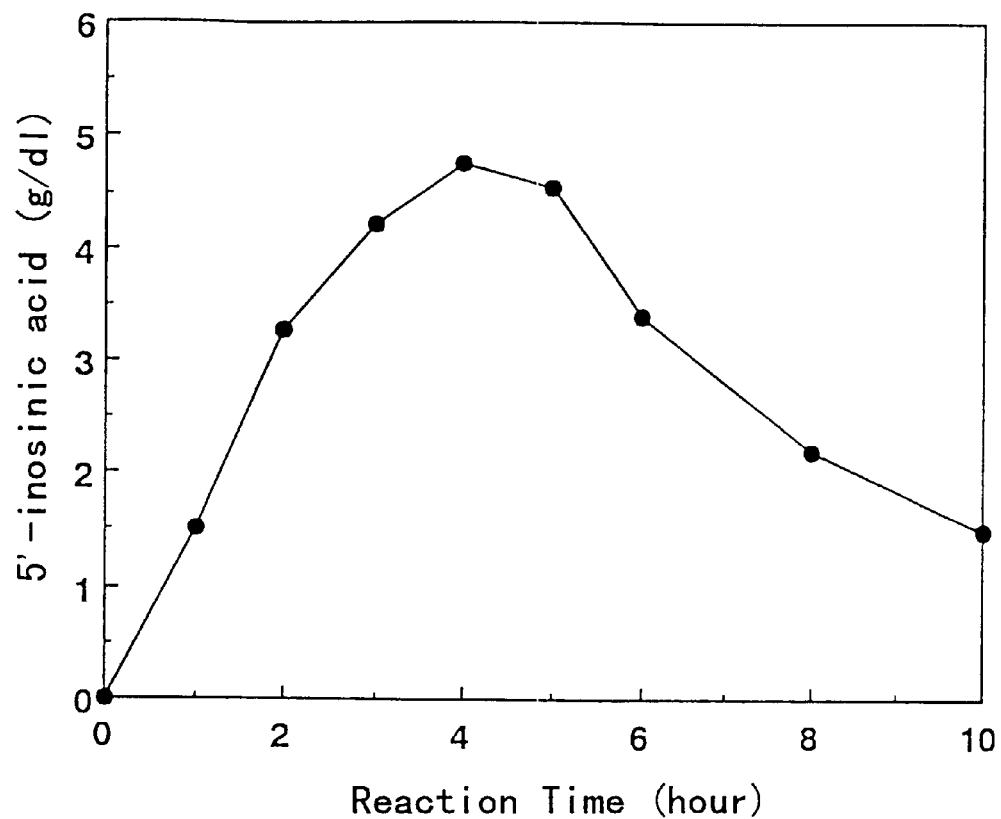

F I G. 9
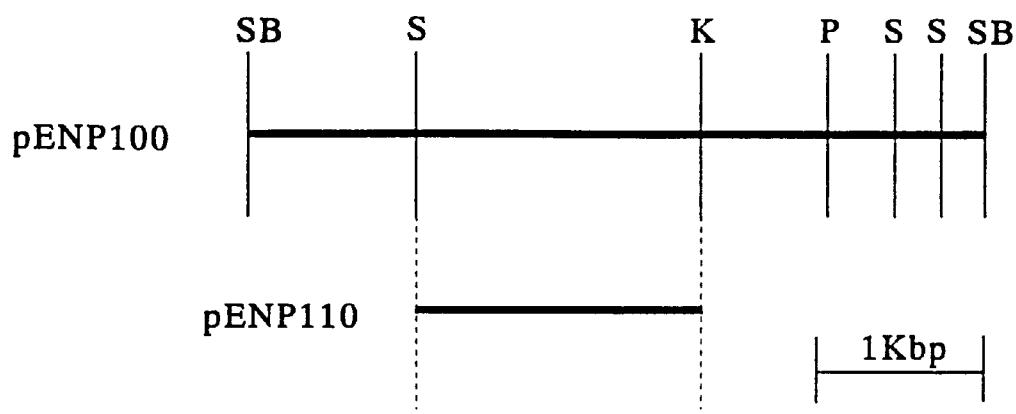
SB: *Sau*3AI / *Bam*HI junction   K: *Kpn*I   P: *Pst*I   S: *Sal*I SB: *Sau*3AI / *Bam*HI junction   E: *Eco*RI   H: *Hin*dIII   K: *Kpn*I
S: *Sac*I SB: Sau3AI / BamHI junction    E: EcoRI    H: HindIII    P: PstI

FIG. 12

```
E.aerogenes    1:MKKRVLALCLASLFSVNAFALVPAGNDATTKPDLYYLKNAQAIDSLALLP  50
E.blattae      1:MKKRVLAVCFAALFSSQALALVATGNDTTTKPDLYYLKNSEAINSLALLP  50
K.planticola   1:MKKRVLALCLASLFSVSAFALVPAGNDATTKPDLYYLKNAQAIDSLALLP  50
M.morganii     1:MKKNIIAGCLFSLFSLSALAAIPAGNDATTKPDLYYLKNEQAIDSLKLLP  50
P.stuartii     1:MKKLLAVFCAGAFVSTSVFAAIPPGNDVTTKPDLYYLKNSQAIDSLALLP  50
S.ficaria      1:MKK-ILLA-TLSCAALTQFS--FAAKDVTTHPEVYFLQESQSIDSLALLP  46
                 ***        * **  * *      *  ** ***

E.aerogenes   51:PPPEVGSIAFLNDQAMYEKGRLLRNTERGKLAAEDANLSAGGVANAFSSA 100
E.blattae     51:PPPAVGSIAFLNDQAMYEQGRLLRNTERGKLAAEDANLSSGGVANAFSGA 100
K.planticola  51:PPPEVGSIAFLNDQAMYEKGRLLRATARGKLAAEDANLSAGGVANAFSGA 100
M.morganii    51:PPPEVGSIQFLNDQAMYEKGRMLRNTERGKQAQADADLAAGGVATAFSGA 100
P.stuartii    51:PPPEVGSILFLNDQAMYEKGRLLRNTERGEQAAKDADLAAGGVANAFSEA 100
S.ficaria     47:PPPAMDSIDFLNDKAQYDAGKIVRNTPRGKQAYDDAHVAGDGVAAAFSNA  96
                 ***   ** **** *  *    *  *      *  **      *** *

E.aerogenes  101:FGSPITEKDAPQLHKLLTNMIEDAGDLATRSAKEKYMRIRPFAFYGVSTC 150
E.blattae    101:FGSPITEKDAPALHKLLTNMIEDAGDLATRSAKDHYMRIRPFAFYGVSTC 150
K.planticola 101:FGSPISEKDAPALHKLLTNMIEDAGDLATRGAKEKYMRIRPFAFYGVSTC 150
M.morganii   101:FGYPITEKDSPELYKLLTNMIEDAGDLATRSAKEHYMRIRPFAFYGTETC 150
P.stuartii   101:FGYPITEKDAPEIHKLLTNMIEDAGDLATRSAKEKYMRIRPFAFYGVATC 150
S.ficaria     97:FGLEIAQRKTPELFKLVMKMREDAGDLATRSAKNHYMRIRPFAFYNEATC 146
                 **  *    *   **    *  ********* ** **********  **

E.aerogenes  151:NTTEQDKLSKNGSYPSGHTSIGWATALVLAEINPQRQNEILKRGYELGES 200
E.blattae    151:NTTEQDKLSKNGSYPSGHTSIGWATALVLAEINPQRQNEILKRGYELGQS 200
K.planticola 151:NTTEQDKLSKNGSYPSGHTSIGWATALVLAEINPQRQNEILKRGYELGES 200
M.morganii   151:NTKDQKKLSTNGSYPSGHTSIGWATALVLAEVNPANQDAILERGYQLGQS 200
P.stuartii   151:NTKDQDKLSKNGSYPSGHTAIGWASALVLSEINPENQDKILKRGYELGQS 200
S.ficaria    147:RPDEESTLSKNGSYPSGHTTIGWATALVLAEINPARQGEILQRGYDMGQS 196
                   *   ********* **** **** *  **  *  **  ***  *  *

E.blattae    201:RVICGYHWQSDVDAARVVGSAVVATLHTNPAFQQQLQKAKAEFAQHQKK  249
K.planticola 201:RVICGYHWQSDVDAARIVGSAVVATLHTNPAFQQQLQKAKDEFAKQQK-  248
M.morganii   201:RVICGYHWQSDVDAARIVGSAAVATLHSDPAFQAQLAKAKQEFAQKSQK  249
E.aerogenes  201:RVICGYHWQSDVDAARIVGSAVVATLHTNPAFQQQLQKAKDEFAKTQK-  248
P.stuartii   201:RVICGYHWQSDVDAARIVASGAVATLHSNPEFQKQLQKAKDEFA-KLKK  248
S.ficaria    197:RVICGYHWQSDVTAARMAASAMVARLHAEPTFAAQLQKAKDEF-NGLKK  244
                 ************ ***          * **  ** ** ***   * **
```

METHOD FOR PRODUCING NUCLEOSIDE-5'-PHOSPHATE ESTER

TECHNICAL FIELD

The present invention relates to a method for producing nucleoside-5'-phosphate ester. The present invention also relates to a novel acid phosphatase, a gene coding for the acid phosphatase, a recombinant DNA containing the gene, and a microorganism harboring the recombinant DNA which are useful to produce nucleoside-5'-phosphate ester. Nucleoside-5'-phosphate ester is useful as a seasoning, a pharmaceutical, and a row material for producing such substances.

BACKGROUND ART

Methods for biochemically phosphorylating nucleoside to produce nucleoside-5'-phosphate ester by using the following phosphate group donors are known, including a method which uses p-nitrophenyphosphoric acid (Japanese Patent Publication No. 39-29858), a method which uses inorganic phosphoric acid (Japanese Patent Publication No. 42-1186), a method which uses polyphosphoric acid (Japanese Patent Laid-open No. 53-56390), a method which uses acetylphosphoric acid (Japanese Patent Laid-open No. 56-82098), and a method which uses adenosine triphosphate (ATP) (Japanese Patent Laid-open No. 63-230094). However, these methods have not been satisfactory to produce nucleoside-5'-phosphate ester efficiently and inexpensively because the substrates to be used are expensive, or because by-products are produced in the reaction.

Thus the present inventors have developed a method for efficiently producing nucleoside-5'-phosphate ester without by-producing 2'-, 3'-nucleotide isomers by allowing cells of a specified microorganism to act under an acidic condition on a nucleoside and a phosphate group donor selected from the group consisting of polyphosphoric acid or a salt thereof, phenylphosphoric acid or a salt thereof, and carbamyl phosphate or a salt thereof (Japanese Patent Laid-open No. 7-231793).

However, even this method has had the following drawbacks. Namely, for example, a part of the substrate is degraded during the reaction due to a nucleoside-degrading activity which unfortunately exists in a slight amount in the cells of the microorganism to be used. Moreover, if the reaction is continued, produced and accumulated nucleoside-5'-phosphate ester is degraded. Therefore, by-products are produced in a reaction solution, and it has been impossible to obtain a sufficient yield. In addition, the reaction cannot be performed if the substrate is added at a high concentration because of a low transphosphorylation activity per microbial cell.

DISCLOSURE OF THE INVENTION

An object of the present invention is to provide a method for inexpensively and efficiently producing nucleoside-5'-phosphate ester. Another object of the present invention is to provide an enzyme, a gene coding for the enzyme, a recombinant DNA containing the gene, and a microorganism harboring the recombinant DNA which are useful for the method for producing nucleoside-5'-phosphate ester.

As a result of various investigations made by the present inventors in order to develop a method for producing nucleoside-5'-phosphate ester which is more efficient than the conventional methods, it has been found out that nucleoside-5'-phosphate ester can be efficiently produced at a high yield by allowing an acid phosphatase purified from a cell-free extract of a microorganism to act under a condition of pH 3.0 to 5.5 on a nucleoside and a phosphate group donor selected from the group consisting of polyphosphoric acid or a salt thereof, phenylphosphoric acid or a salt thereof, and carbamyl phosphate or a salt thereof. Further, the present inventors have succeeded in obtaining wild type genes coding for acid phosphatases from various bacteria and genes coding for acid phosphatases having lowered phosphomonoesterase activities from bacterium belonging to the genus Morganella and bacterium belonging to the genus Escherichia. Moreover, the present inventors have found out that productivity of nucleoside-5'-phosphate ester is remarkably improved by expressing the gene in a large amount in accordance with genetic engineering techniques. Thus the present invention has been completed.

Namely, the present invention provides a method for producing nucleoside-5'-phosphate ester comprising the steps of allowing an acid phosphatase, preferably an acid phosphatase having a lowered phosphomonoesterase activity to act under a condition of pH 3.0 to 5.5 on a nucleoside and a phosphate group donor selected from the group consisting of polyphosphoric acid or a salt thereof, phenylphosphoric acid or a salt thereof, and carbamyl phosphate or a salt thereof to produce nucleoside-5'-phosphate ester, and collecting it.

In another aspect, the present invention provides mutant acid phosphatases having a lowered phosphomonoesterase activity, genes coding for the acid phosphatases, recombinant DNAs containing the genes, and microorganisms harboring the recombinant DNA.

In still another aspect, the present invention provides novel acid phosphatases derived from bacteria belonging to the genus Escherichia, Enterobacter, Klebsiella or Serratia, genes coding for the acid phosphatases, recombinant DNAs containing the genes, and microorganisms harboring the recombinant DNA.

The present invention will be explained in detail below.

<1> Preparation of acid phosphatase

The acid phosphatase to be used in the present invention is not specifically limited provided that it catalyzes the reaction to produce nucleoside-5'-phosphate ester by phosphate group transfer to the nucleoside from the phosphate group donor selected from the group consisting of polyphosphoric acid or a salt thereof, phenylphosphoric acid or a salt thereof, and carbamyl phosphate or a salt thereof under the condition of pH 3.0 to 5.5. Such an acid phosphatase preferably includes those derived from microorganisms. In an especially preferred embodiment, the present invention uses an enzyme derived from a bacterium belonging to the genus Morganella, Escherichia, Providencia, Enterobacter, Klebsiella or Serratia. Representative examples of such a bacterium include the following bacterial strains.

*Morganella morganii* NCIMB 10466
*Morganella morganii* IFO 3168
*Morganella morganii* IFO 3848
*Escherichia blattae* JCM 1650
*Escherichia blattae* ATCC 33429
*Escherichia blattae* ATCC 33430
*Providencia stuartii* ATCC 29851
*Providencia stuartii* ATCC 33672
*Enterobacter aerogenes* IFO 12010
*Enterobacter aerogenes* IFO 13534
*Klebsiella planticola* IFO 14939

*Klebsiella planticola* IAM 1133
*Serratia ficaria* IAM 13540
*Serratia marcescens* IAM 12143

It is noted that acid phosphatase (EC 3.1.3.2) is originally an enzyme which catalyzes a reaction to hydrolyze phosphate ester under an acidic condition, and it has a nucleotidase activity to degrade nucleoside-5'-phosphate ester produced by the transphosphorylation reaction (hereinafter, the nucleotidase activitiy is referred to as "phosphomonoesterase activity"). Even such an acid phosphatase can be used in the method for producing nucleoside-5'-phosphate ester of the present invention. However, in order to obtain nucleoside-5'-phosphate ester at a high yield, it is desirable to use the mutant acid phosphatase in which the phosphomonoesterase activity is lowered as compared with the wild type acid phosphatase produced by the bacteria as described above (hereinafter simply referred to as "mutant acid phosphatase", if necessary).

The mutant acid phosphatase is obtained by expressing a mutant gene obtained by directly mutating a gene coding for an acid phosphatase as described below. Alternatively, the mutant acid phosphatase may be also obtained by treating a microorganism which produces an acid phosphatase with irradiation of ultraviolet light or a mutating agent usually used for artificial mutation such as N-methyl-N'-nitro-N-nitrosoguanidine (NTG), and cultivating a microorganism mutated to produce a mutant acid phosphatase having a lowered phosphomonoesterase activity.

A protein having the acid phosphatase activity may be obtained from the microorganisms as described above by cultivating the microbial strain having the activity in an appropriate medium, harvesting proliferated microbial cells, disrupting the microbial cells to prepare a cell-free extract, and adequately purifying the protein therefrom.

The medium for cultivating the microorganism is not specifically limited, for which an ordinary medium may be available, containing an ordinary carbon source, a nitrogen source, inorganic ions, and optionally an organic nutrient source. The carbon source to be adequately used includes, for example, saccharides such as glucose and sucrose, alcohols such as glycerol, and organic acids. The nitrogen source to be used includes, for example, ammonia gas, aqueous ammonia, and ammonium salts. The inorganic ions to be adequately used if necessary include, for example, magnesium ion, phosphate ion, potassium ion, iron ion, and manganese ion. The organic nutrient source to be adequately used includes, for example, vitamins and amino acids as well as those containing them such as yeast extract, peptone, meat extract, corn steep liquor, casein hydrolysate, and soybean hydrolysate.

The cultivation condition is also not specifically limited. The microorganism may be cultivated, for example, under an aerobic condition for about 12 to 48 hours while appropriately controlling pH and temperature within ranges of pH 5 to 8 and temperature of 25° to 40° C.

Proliferated microbial cells may be harvested from a culture liquid, for example, by centrifugation. The cell-free extract is prepared from the harvested microbial cells by using an ordinary method. Namely, the cell-free extract is obtained by disrupting the microbial cells by means of a method such as ultrasonic treatment, Dyno-mill, and French Press, and removing cell debris by centrifugation.

The acid phosphatase is purified from the cell-free extract by using an adequate combination of techniques usually used for enzyme purification such as ammonium sulfate fractionation, ion exchange chromatography, hydrophobic chromatography, affinity chromatography, gel filtration chromatography, and isoelectric purification. As for the precipitation, it is not necessarily indispensable to completely purify the acid phosphatase. It is sufficient to achieve removal of contaminants such as an enzyme which participates in degradation of nucleoside as the substrate.

<2> Preparation of acid phosphatase gene

A DNA fragment, which contains a structural gene coding for the protein having the acid phosphatase activity, can be cloned starting from, for example, cells of the microorganism having the enzyme activity. The cloning method includes, for example, a method in which a chromosomal gene expression library is screened by using the enzyme activity as an index, a method in which an antibody against the protein is prepared to screen a chromosomal gene expression library, and a method in which an amino acid sequence such as an N-terminal sequence of the purified protein is analyzed, on the basis of which a probe is prepared to screen a gene library.

Specifically, the gene coding for the acid phosphatase of *Morganella morganii*, *Escherichia blattae*, *Providencia stuartii*, *Enterobacter aerogenes*, *Klebsiella planticola*, *Serratia ficaria* or *Serratia marcescens* described above can be cloned by preparing a chromosomal gene expression library of each of the microorganisms, and screening the library by using the phosphatase activity as an index.

Namely, a chromosomal gene expression library can be prepared by firstly preparing chromosomal DNA from the above bacteria, partially degrading it with an appropriate restriction enzyme, subsequently ligating it with a vector autonomously replicable in *Escherichia coli*, and transforming *Escherichia coli* with the obtained recombinant DNA. A wide variety of restriction enzymes can be used for digesting chromosomal DNA by adjusting the digestion reaction time to adjust the degree of digestion. Any vector may be used for cloning the gene provided that it is autonomously replicable in *Escherichia coli*. It is possible to use, for example, pUC19, pUC118, pHSG298, pBR322, and pbluescript II.

The vector may be ligated with the DNA fragment containing the gene coding for the acid phosphatase to prepare the recombinant DNA by previously digesting the vector with the same restriction enzyme as that used for digesting chromosomal DNA, or with a restriction enzyme which generates a cleaved edge complementary with a cleaved edge of the chromosomal DNA fragment, and ligating it with the DNA fragment by using ligase such as T4 DNA ligase. Any microbial strain may be used as a recipient for the prepared recombinant DNA provided that it is appropriate for replication of the vector. It is possible to use, for example, microbial strains of *Escherichia coli* such as HB101, JM109, and DH5.

Transformants thus obtained are grown on an agar medium to form their colonies. After that, when a reaction solution containing p-nitrophenylphosphoric acid is poured onto a surface of the medium to perform a reaction, then a strain, which has expressed the phosphatase activity, liberates p-nitrophenol and exhibits a yellow color. A transformant, which harbors a DNA fragment containing the gene coding for the objective acid phosphatase, can be selected by performing the reaction described above under an acidic condition, and selecting the transformant by using the color development as an index.

After that, a recombinant DNA is recovered from the selected transformant to analyze the structure of the DNA fragment containing the gene coding for the acid phosphatase ligated with the vector. A nucleotide sequence of the gene coding for the acid phosphatase is shown in SEQ ID NO: 2 in Sequence Listing in the case of a gene derived from Morganella morganii NCIMB 10466, SEQ ID NO: 9 in Sequence Listing in the case of a gene derived from *Escherichia blattae* JCM 1650, SEQ ID NO: 17 in Sequence Listing in the case of a gene derived from *Providencia stuartii* ATCC 29851, SEQ ID NO: 19 in Sequence Listing in the case of a gene derived from *Enterobacter aerogenes* IFO 12010, SEQ ID NO: 21 in Sequence Listing in the case of a gene derived from *Klebsiella planticola* IFO14939, or SEQ ID NO: 23 in Sequence Listing in the case of a gene derived from *Serratia ficaria* IAM 13540.

The deduced amino acid sequences of the acid phosphatases encoded by the above genes are illustrated in SEQ ID NO: 4, 11, 18, 20, 22 and 24. The acid phosphatases encoded by the above genes are prefferably used for the present invention. In addition, the acid phosphatase comprising an amino acid sequence which is substantially identical with an amino acid sequence of any one of the acid phosphatases encoded by the above genes is also prefferably used for the present invention. The term "substantially identical" means that amino acid sequences of the acid phosphatases may have substitution, deletion, insertion or transition of one or a plurality of amino acid residues without losing an activity to produce nucleoside-5'-phosphate ester (hereinafter referred to as "transphosphorylation activity").

<3> Preparation of gene coding for mutant acid phosphatase

The wild type acid phosphatase obtained as described above has a phosphomonoesterase activity. Therefore, the phosphomonoesterase activity may serve as a factor to cause accompanying degradation of the product as the reaction time passes in the production of nucleoside-5'-phosphate ester, resulting in decrease in reaction yield. In order to overcome such a circumstance, it is advantageous to cause artificial mutation on the gene coding for the acid phosphatase so that the phosphomonoesterase activity is lowered.

Methods for site-directed mutagenesis for causing objective mutation at an objective site of DNA include, for example, a method to use PCR (Higuchi, R., 61, in *PCR technology*, Erlich, H. A. Eds., Stockton press (1989); Carter, P., *Meth. in Enzymol.*, 154, 382 (1987)), and a method to use phage (Kramer, W. and Frits, H. J., *Meth. in Enzymol.*, 154, 350 (1987); Kunkel, T. A. et al., *Meth. in Enzymol.*, 154, 367 (1987)).

The mutant acid phosphatase having the lowered phosphomonoesterase activity is exemplified by the acid phosphatase comprising an amino acid sequence which is substantially identical with an amino acid sequence selected from the group consisting of sequences illustrated in SEQ ID NOs: 4, 11, 18, 20, 22 and 24 in Sequence Listing, and has mutation which lowers phosphomonoesterase activity of wild type acid phosphatase. Concretely, the mutant acid phosphatase having the lowered phosphomonoesterase activity is exemplified, for the enzyme derived from *Morganella morganii* NCIMB 10466, by one in which the 72th glycine residue and/or the 151th isoleucine residue is substituted with another amino acid residue in an amino acid sequence illustrated in SEQ ID NO: 4 in Sequence Listing. In Examples described below, a gene coding for a mutant acid phosphatase is illustrated as an example in which the 72th glycine residue is substituted with an aspartic acid residue, and the 151th isoleucine residue is substituted with a threonine residue. On the other hand, the acid phosphatase having the lowered phosphomonoesterase activity is exemplified, for the enzyme derived from *Escherichia blattae* JCM 1650, by one in which the 74th glycine residue and/or the 153th isoleucine residue is substituted with another amino acid residue in an amino acid sequence illustrated in SEQ ID NO: 11 in Sequence Listing. In Examples described below, a gene coding for mutant acid phosphatase is illustrated as an example in which the 74th glycine residue is substituted with an aspartic acid residue, and the 153th isoleucine residue is substituted with a threonine residue.

Therefore, the nucleotide may be substituted at the specified site of the wild type gene in accordance with the site-directed mutagenesis method described above so that these mutant acid phosphatases are encoded. The mutation to lower the phosphomonoesterase activity is desirably a type of mutation by which the activity to produce nucleoside-5'-phosphate ester is not substantially lowered in comparison with wild type acid phosphatase. However, even in the case that the activity to produce nucleoside-5'-phosphate ester is lowrerd, it will be sufficient if degree of decrease of phosphomonoesterase activity is larger than that of the activity to produce nucleoside-5'-phosphate ester, with the result that a ratio of phosphomonoesterase activity to the activity to produce nucleoside-5'-phosphate ester of the mutant acid phosphatase is lowered in comparison with the wild type acid phosphatase. As for the degree of decrease in the phosphomonoesterase activity, the activity may be decreased to less than about 40% of that of the wild type enzyme. As illustrated below in the embodiments, the amino acid sequence of the acid phosphatase of *Escherichia blattae* JCM 1650 is highly homologous to that of *Morganella morganii* NCIMB 10466, and the 72th glycine residue and the 151th isoleucine residue in an amino acid sequence illustrated in SEQ ID NO: 4 correspond to the 74th glycine residue and the 153th isoleucine residue in an amino acid sequence illustrated in SEQ ID NO: 11 respectively. Further, in addition to *Escherichia blattae* JCM 1650, amino acid sequences of acid phosphatases derived from microorganisms such as *Providencia stuartii* ATCC 29851, *Enterobacter aerogenes* IFO 12010, *Klebsiella planticola* IFO 14939, and *Serratia ficaria* IAM 13450 have high homology with that of *Morganella morganii* NCIMB 10466, and amino acid sequences of these acid phosphatases include amino acids resudues each of which corresponds to the 72th glycine residue and the 151th isoleucine residue in an amino acid sequence illustrated in SEQ ID NO: 4 respectively. Therefore, genes coding for mutant acid phosphatases derived from these microorganisms may be obtained as described above. The 92th glycine residue and the 171th isoleucine residue in the amino acid sequence of the acid phosphatase derived from *Providencia stuartii* ATCC 29851, *Enterobacter aerogenes* IFO 12010 or *Klebsiella planticola* IFO 14939 illustrated in SEQ ID NO: 18, 20 or 22, and the 88th glycine residue and the 167th isoleucine residue in the amino acid sequence of the acid phosphatase derived from *Serratia ficaria* IAM 13450 illustrated in SEQ ID NO: 24 respectively correspond to the 72th glycine residue and the 151th isoleucine residue in an amino acid sequence illustrated in SEQ ID NO: 4.

<4> Introduction of acid phosphatase gene into host

A recombinant microorganism for expressing the acid phosphatase activity at a high level can be obtained by introducing the DNA fragment containing the gene coding for the protein having the acid phosphatase activity obtained as described above into cells of a host after recombining the DNA fragment again with an appropriate vector. In such a procedure, the wild type acid phosphatase is expressed by using the gene coding for the wild type acid phosphatase, while the mutant acid phosphatase is expressed by using the gene coding for the mutant acid phosphatase.

The host includes the microbial strains of *Escherichia coli* such as HB101, JM109, and DH5 described above. Other than these strains, all bacteria can be utilized as the host provided that a replication origin of constructed recombinant DNA and the acid phosphatase gene make their functions, the recombinant DNA is replicable, and the acid phosphatase gene is expressible. One of the most preferred hosts is *Escherichia coli* JM109.

The vector for incorporating the gene coding for the acid phosphatase thereinto is not specifically limited provided that it is replicable in the host. When *Escherichia coli* is used as the host, the vector may be exemplified by plasmids autonomously replicable in this bacterium. For example, it is possible to use ColE1 type plasmids, p15A type plasmids, R factor type plasmids, and phage type plasmids. Such plasmids specifically include, for example, pBR322 (*Gene*, 2, 95 (1977)), pUC19 (Gene, 33, 103 (1985)), pUC119 (*Methods in Enzymology*, 153, 3 (1987)), pACYC184 (*J. Bacteriol.*, 134, 1141 (1978)), and pSC101 (*Proc. Natl. Acad. Sci. U.S.A.*, 70, 3240 (1973)).

When the DNA fragment containing the gene coding for the acid phosphatase contains a promoter which is functional in the host, the DNA fragment may be ligated with the vector as it is. When the DNA fragment does not contain such a promoter, another promoter which works in the host microorganism such as lac, trp, and PL may be ligated at a position upstream from the gene. Even when the DNA fragment contains the promoter, the promoter may be substituted with another promoter in order to efficiently express the gene coding for the acid phosphatase.

There is no special limitation for a method for introducing, into the host, the recombinant DNA constructed by ligating the vector with the DNA fragment containing the gene coding for the acid phosphatase. The recombinant DNA may be introduced into the host by using an ordinary method. When *Escherichia coli* is used as the host, it is possible to use, for example, a calcium chloride method (*J. Mol. Biol.*, 53, 159 (1970)), a method of Hanahan (*J. Mol. Biol.*, 166, 557 (1983)), an SEM method (*Gene*, 96, 23 (1990)), a method of Chung et al. (*Proc. Natl. Acad. Sci. U.S.A.*, 86, 2172 (1989)), and electroporation (*Nucleic Acids Res.*, 16, 6127 (1988)).

The acid phosphatase gene may be inserted into the autonomously replicable vector DNA, which may be introduced into the host so that it is harbored by the host as extrachromosomal DNA as described above. Alternatively, the acid phosphatase gene may be incorporated into chromosome of the host microorganism in accordance with a method which uses transduction, transposon (*Biotechnol.*, 1, 417 (1983)), Mu phage (Japanese Patent Laid-open No. 2-109985), or homologous recombination (*Experiments in Molecular Genetics*, Cold Spring Harbor Lab. (1972)).

<5> Expression of acid phosphatase gene by recombinant microorganism

The transformant obtained as described above, into which the recombinant DNA containing the gene coding for the acid phosphatase has been introduced, is capable of expressing the acid phosphatase activity at a high level in its cells by cultivating it in an appropriate medium containing a carbon source, a nitrogen source, inorganic ions, and optionally an organic nutrient source. The carbon source to be adequately used includes, for example, carbohydrates such as glucose, alcohols such as glycerol, and organic acids. The nitrogen source to be used includes, for example, ammonia gas, aqueous ammonia, and ammonium salts. The inorganic ions to be adequately used if necessary include, for example, magnesium ion, phosphate ion, potassium ion, iron ion, and manganese ion. The organic nutrient source to be adequately used includes, for example, vitamins and amino acids as well as those containing them such as yeast extract, peptone, meat extract, corn steep liquor, casein hydrolysate, and soybean hydrolysate. The amount of expression of the acid phosphatase activity may be increased by adding, to the medium, an expression-inducing agent depending on a promoter such as IPTG (isopropyl-$\beta$-D-thiogalactopyranoside).

The cultivation condition is also not specifically limited. The cultivation may be performed, for example, under an aerobic condition for about 12 to 48 hours while appropriately controlling pH and temperature within ranges of pH 5 to 8 and temperature of 25° to 40° C.

After that, microbial cells are harvested from a culture, and a cell-free extract is obtained by disruption, from which the acid phosphatase can be purified. The purification is performed by using an appropriate combination of techniques usually used for enzyme purification such as those described in the aforementioned item <1>. As for the purification, it is not necessarily indispensable to completely purify the acid phosphatase. It is sufficient to achieve removal of contaminants such as an enzyme which participates in degradation of nucleoside as the substrate.

<6> Production of nucleoside-5'-phosphate ester

Nucleoside-5'-phosphate ester can be produced in a reaction mixture by allowing the acid phosphatase obtained as described in the item <1>, or the wild type acid phosphatase or the mutant acid phosphatase obtained by expressing the gene in a large amount in accordance with the genetic engineering technique as described in the item <5> to make contact and cause the reaction of a nucleoside with a phosphate group donor selected from the group consisting of polyphosphoric acid or a salt thereof, phenylphosphoric acid or a salt thereof, and carbamyl phosphate or a salt thereof. In order to achieve a high productivity in this reaction, it is important to adjust pH of the reaction solution to be weakly acidic in a range of 3.0 to 5.5.

When the gene coding for the acid phosphatase is expressed in a large amount by means of the genetic engineering technique, especially when the gene coding for the mutant acid phosphatase having the lowered phosphomonoesterase activity is expressed in a large amount, then it is also possible to produce nucleoside-5'-phosphate ester inexpensively and efficiently by using a culture containing microbial cells of the transformant, the microbial cells separated and harvested from the culture, or a product obtained from the microbial cells in accordance with, for example, an immobilizing treatment, an acetone treatment, or a lyophilizing treatment, instead of the purified acid phosphatase.

The nucleoside to be used includes, for example, purine nucleosides such as inosine, guanosine, adenosine, xanthosine, purine riboside, 6-methoxypurine riboside, 2,6-diaminopurine riboside, 6-fluoropurine riboside, 6-thiopurine riboside, 2-amino-6-thiopurine riboside, and mercaptoguanosine; and pyrimidine nucleosides such as uridine, cytidine, 5-aminouridine, 5-hydroxyuridine, 5-bromouridine, and 6-azauridine. As a result of the reaction, these natural type nucleosides and nonnatural type nucleosides are specifically phosphorylated at their 5'-positions, and corresponding nucleoside-5'-phosphate esters are produced respectively.

The nucleoside is desirably added to the reaction solution at a concentration of 1 to 20 g/dl. In the case of use of a nucleoside which is scarcely soluble in water, the reaction yield may be improved by adding boric acid or a surfactant such as dimethyl sulfoxide.

As for the phosphate group donor to be used, those usable as the polyphosphoric acid or the salt thereof include, for example, pyrophosphoric acid, tripolyphosphoric acid, trimetaphosphoric acid, tetrametaphosphoric acid, hexametaphosphoric acid, mixtures thereof, sodium salts thereof, potassium salts thereof, and mixtures of these salts. Those usable as the phenylphosphoric acid or the salt thereof include, for example, disodium phenylphosphate, dipotassium phenylphosphate, O,O-diphenylphosphoric acid anhydride, and mixtures thereof. Those usable as the carbamyl phosphate or the salt thereof include, for example, disodium carbamyl phosphate, dipotassium carbamyl phosphate, diammonium carbamyl phosphate, dilithium carbamyl phosphate, and mixtures thereof. The concentration at which the phosphate group donor is used is determined by the concentration of the nucleoside as the phosphate group acceptor. The phosphate group donor is usually used in an amount which is 1 to 5 times that of the nucleoside.

A preferred result is obtained in the reaction usually at a temperature of 20° to 60° C., preferably 30° to 40° C. at a pH on a weakly acidic side of 3.5 to 6.5, preferably 4.0 to 5.0. The reaction may be performed by adopting any one of a stationary method and an agitating method. The reaction time defers depending on the condition such as the activity of the enzyme to be used and the substrate concentration, however, it is 1 to 100 hours.

The nucleoside-5'-phosphate ester thus produced may be collected and separated from a mixture after completion of the reaction by adopting a method to use a synthetic resin for adsorption, a method to use a precipitating agent, and other ordinary methods for collection and separation.

BRIEF DESCRIPTION OF THE DRAWINGS

FIG. 6 illustrates a restriction enzyme map of a chromosomal DNA fragment of *Escherichia blattae* containing a gene coding for an acid phosphatase.

FIG. 7 illustrates a diagram showing produced amount of 5'-inosinic acid in a reaction performed by using a strain harboring the acid phosphatase gene derived from *Escherichia blattae*.

FIG. 9 illustrates a restriction enzyme map of a chromosomal DNA fragment derived from *Enterobacter aerogenes* which contains the gene coding for acid phosphatase.

FIG. 12 illustrates amino acid sequences in one-letter deduced from nucleotide sequences of acid phosphatases derived from *Morganella morganii*, *Escherichia blattae*, *Providencia stuartii*, *Enterobacter aerogenes*, *Klebsiella planticola* and *Serratia ficaria*.

DESCRIPTION OF PREFERRED EMBODIMENTS

Figure 1:
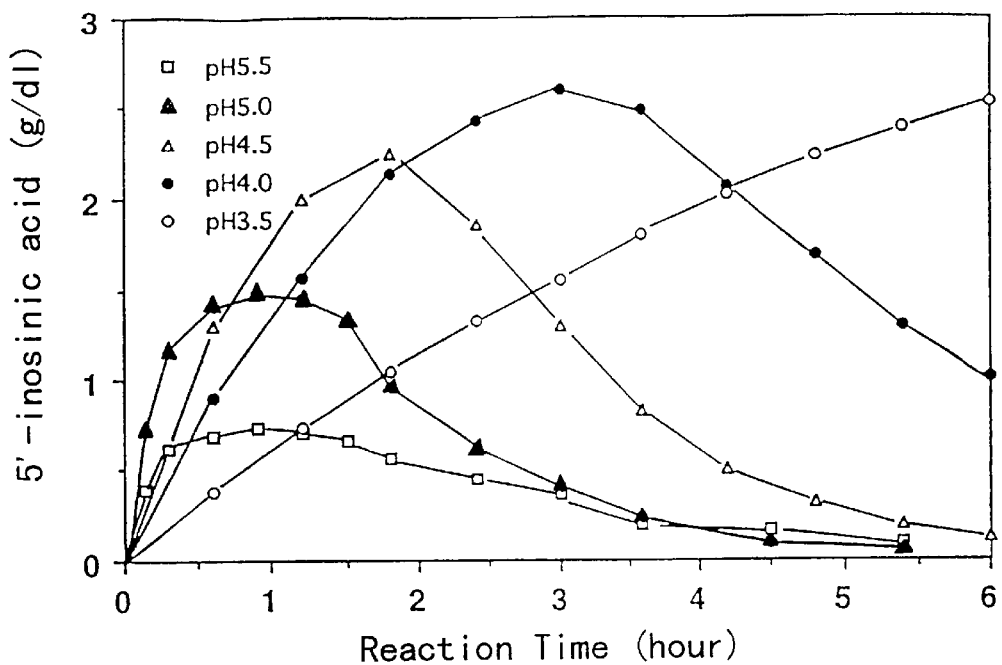
FIG. 1 illustrates a relationship between reaction pH and produced amount of 5'-inosinic acid in a reaction performed by using an enzyme derived from *Morganella morganii*.

The present invention will be specifically explained below with reference to Examples, however, the present invention is not limited to these Examples.

The transphosphorylation activity was measured under the following condition using inosine as a substrate. The reaction was performed at pH 5.0 at 30° C. for 10 minutes in a reaction solution (1 ml) containing 40 $\mu$mol/ml of inosine, 100 $\mu$mol/ml of sodium pyrophosphate, 100 $\mu$mol/ml of sodium acetate buffer (pH 5.0), and an enzyme. The reaction was stopped by adding 200 $\mu$l of 2 N hydrochloric acid. After that, precipitates were removed by centrifugation. Then, 5'-Inosinic acid produced by the transphosphorylation reaction was quantitatively measured. An amount of enzyme to produce 1 $\mu$mol of 5'-inosinic acid per 1 minute under this standard reaction condition was defined as 1 unit.

The phosphomonoesterase activity was measured under the following condition using 5'-inosinic acid as a substrate. The reaction was performed at 30° C. for 10 minutes in a reaction solution (1 ml) containing 10 $\mu$mol/ml of 5'-inosinic acid, 100 $\mu$mol/ml of MES/NaOH buffer (pH 6.0), and an enzyme. The reaction was stopped by adding 200 $\mu$l of 2 N hydrochloric acid. After that, precipitates were removed by centrifugation. Then, inosine produced by the hydrolytic reaction was quantitatively measured. An amount of enzyme to produce 1 $\mu$mol of inosine per 1 minute under this standard reaction condition was defined as 1 unit.

Inosine and 5'-inosinic acid were analyzed under the following condition by means of high-performance liquid chromatography (HPLC).

Column: Cosmosil 5C18-AR (4.6×150 mm) [produced by nacalai tesque];

Mobile phase: 5 mM potassium phosphate buffer (pH 2.8)/methanol=95/5;

Flow rate: 1.0 ml/min;

Temperature: room temperature;

Detection: UV 245 nm.

Incidentally, in the reaction to produce nucleoside-5'-phosphate esters using nucleosides other than inosine as raw materials, the nucleosides as raw materials and produced nucleoside-5'-phosphate esters were analyzed by HPLC as described above.

EXAMPLE 1

Purification and Caracterozatoion of Acid Phosphatase Derived from *Morganella morganii*

A nutrient medium (pH 7.0, 50 ml) containing 1 g/dl of peptone, 0.5 g/dl of yeast extract, and 1 g/dl of sodium chloride was poured into Sakaguchi flasks (500 ml), which was sterilized at 120° C. for 20 minutes. A slant culture of *Morganella morganii* NCIMB 10466 was inoculated to each of the flasks once with a platinum loop, which was cultivated at 30° C. for 16 hours with shaking. Microbial cells (about 3,000 g), which were harvested from a culture by centrifugation, were suspended in 100 mM potassium phosphate buffer (1 L, pH 7.0). A ultrasonic treatment was performed at 4° C. for 20 minutes to disrupt the microbial cells. The treated suspension was centrifuged to remove its insoluble fraction. Thus a cell-free extract was prepared.

Ammonium sulfate was added to the cell-free extract so that 30% saturation was achieved. Appeared precipitate was removed by centrifugation, and then ammonium sulfate was further added to supernatant so that 60% saturation was achieved. Appeared precipitate was collected by centrifugation, and it was dissolved in 100 mM potassium phosphate buffer.

This crude enzyme solution was dialyzed four times against 5 L of 100 mM potassium phosphate buffer (pH 7.0), and then it was applied to a DEAE-Toyopeal 650M column (φ4.1×22 cm) equilibrated with 20 mM potassium phosphate buffer (pH 7.0), followed by washing with 800 ml of 20 mM potassium phosphate buffer (pH 7.0). The transphosphorylation activity was found in a fraction which passed through the column, and thus the fraction was recovered.

The fraction was added with ammonium sulfate so that 35% saturation was achieved, which was adsorbed to a Butyl-Toyopeal column (φ3.1×26 cm) equilibrated with 20 mM potassium phosphate buffer (pH 7.0) containing ammonium sulfate at 35% saturation. Elution was performed by using a linear concentration gradient from 35% saturation to 20% saturation in potassium phosphate buffer (pH 7.0).

Active fractions were collected and dialyzed against 1 L of 50 mM potassium phosphate buffer (pH 7.0), followed by being applied to a hydroxyapatite column (φ5×6.5 cm) equilibrated with 50 mM potassium phosphate buffer (pH 7.0). Elution was performed by using a linear concentration gradient from 50 mM to 300 mM of potassium phosphate buffer (pH 7.0).

Active fractions were collected and concentrated by ultrafiltration. This enzyme solution was applied into a HiLoad TM 16/60 Superdex 200 column (produced by Pharmacia). Elution was performed at a flow rate of 1.0 ml/minute by using 50 mM potassium phosphate buffer containing 100 mM sodium chloride.

In accordance with the procedure as described above, the enzyme exhibiting the transphosphorylation activity was purified from the cell-free extract consequently about 550-fold at a recovery ratio of about 10%. The specific activity and the recovery ratio in this purification process are shown in Table 1. This enzyme sample was homogeneous on SDS-polyacrylamide gel electrophoresis.

TABLE 1

| Step Recovery | Total activity (unit) | Total protein (mg) | Specific activity (unit/mg) | ratio (%) |
|---|---|---|---|---|
| 1. Cell-free extract | 597 | 127,200 | 0.005 | 100 |
| 2. Ammonium sulfate fractionation (30 to 60%) | 568 | 122,210 | 0.005 | 95 |
| 3. DEAE-Toyopearl | 517 | 36,498 | 0.014 | 87 |
| 4. Butyl-Toyopearl | 394 | 1,121 | 0.351 | 66 |
| 5. Hydroxyapatite | 112 | 50 | 2.244 | 19 |
| 6. Superdex 200 | 63 | 24 | 2.630 | 10 |

The purified enzyme had the following properties.

(1) Action: Phosphate group is transferred from a phosphate group donor such as polyphosphoric acid to nucleoside, and nucleoside-5'-phosphate ester is produced. Reversely, this enzyme also exhibits an activity to hydrolyze phosphate ester.

(2) Substrate specificity: Those which serve as the phosphate group donor in the transphosphorylation reaction include, for example, pyrophosphoric acid, tripolyphosphoric acid, trimetaphosphoric acid, tetrametaphosphoric acid, hexametaphosphoric acid, disodium phenylphosphate, dipotassium phenylphosphate, O,O-diphenylphosphoric acid anhydride, disodium carbamyl phosphate, dipotassium carbamyl phosphate, diammonium carbamyl phosphate, and dilithium carbamyl phosphate. Those which serve as the phosphate group acceptor include, for example, purine riboside, inosine, guanosine, adenosine, xanthosine, uridine, and cytidine. On the other hand, those which undergo the action in the phosphate ester hydrolytic reaction include, for example, inorganic phosphoric acid such as pyrophosphoric acid, tripolyphosphoric acid, trimetaphosphoric acid, tetrametaphosphoric acid, hexametaphosphoric acid; phosphate ester such as disodium phenylphosphate, dipotassium phenylphosphate, O,O-diphenylphosphoric acid anhydride, disodium carbamyl phosphate, dipotassium carbamyl phosphate, diammonium carbamyl phosphate, and dilithium carbamyl phosphate; and 5'-nucleotide such as 5'-purine ribotide, 5'-inosinic acid, 5'-guanylic acid, 5'-adenylic acid, 5'-xanthylic acid, 5'-uridylic acid, and 5'-cytidylic acid.

(3) Optimum pH: 5.2 (transphosphorylation reaction), 6.5 (phosphate ester hydrolytic reaction).

(4) pH stability: pH 3.0 to 12.0 (treatment at 30° C. for 60 minutes).

(5) Optimum temperature: about 35° C.

(6) Temperature stability: stable up to 30° C. (treatment at pH 7.0 for 30 minutes).

(7) Effect of the addition of metal ion and inhibitor: This enzyme exhibits no activation phenomenon relevant to its activity by addition of any metal ion. The activity is inhibited by $Ag^{2+}$, $Pb^{2+}$, $Hg^{2+}$, and $Cu^{2+}$. The activity is also inhibited by iodoacetic acid.

(8) Molecular weight: A calculated molecular weight is about 190,000 in accordance with high-performance liquid chromatography (TSKgel G-3000SW, produced by Toyo Soda).

(9) Subunit molecular weight: A calculated subunit molecular weight is about 25,000 in accordance with SDS-polyacrylamide gel electrophoresis.

This enzyme exhibits not only the activity to transfer phosphate group to nucleoside, but also the activity to reversely hydrolyze phosphate ester. Moreover, this enzyme exhibits the phosphate ester hydrolytic activity (phosphomonoestrase activity) which is higher than the transphosphorylation activity by not less than 20 times. Other properties are well coincident with those of a known acid phosphatase produced by a bacterium belonging to the genus Morganella (*Microbiology*, 140, 1341–1350 (1994)). Accordingly, it has been clarified that this enzyme is an acid phosphatase.

Sodium pyrophosphate (10 g/dl) and inosine (2 g/dl) were dissolved in sodium acetate buffers each having pH of 5.5, 5.0, 4.5, 4.0, and 3.5, to which the enzyme sample described above was added so that a concentration of 50 units/dl was obtained. The reaction mixture was incubated at 30° C. for 6 hours while maintaining each pH, and the amount of produced 5'-inosinic acid was measured along with passage of time. Produced inosinic acid contained only 5'-inosinic acid. By-production of 2'-inosinic acid and 3'-inosinic acid was not observed at all. A result is shown in FIG. 1. The velocity of 5'-inosinic acid production was maximum at pH 5.0. However, the maximum accumulated amount of 5'-inosinic acid was higher at lower pH. The reaction condition at pH 4.0 was most efficient for production of 5'-inosinic acid, in which 5'-inosinic acid was produced and accumulated in an amount of 2.60 g/dl by performing the reaction for 3 hours.

EXAMPLE 2
Phosphorylation Reaction of Various Nucleosides by Acid Phosphatase Sample Derived from *Morganella morganii*

Sodium pyrophosphate (10 g/dl) and inosine, guanosine, uridine, or cytidine (2 g/dl) as a phosphate group acceptor were dissolved in sodium acetate buffer (pH 4.0), to which the enzyme sample prepared in Example 1 was added so that its concentration was 50 units/dl. The reaction mixture was incubated at 30° C. for 3 hours while maintaining pH at 4.0. The amount of nucleoside-5'-ester produced by the reaction is shown in Table 2.

Produced nucleotide contained only nucleoside-5'-ester. By-production of nucleoside-2'-ester and nucleoside-3'-ester was not observed at all.

TABLE 2

| Nucleoside | Product | Produced amount (g/dl) |
| --- | --- | --- |
| Inosine | 5'-inosinic acid | 2.60 |
| Guanosine | 5'-guanylic acid | 1.90 |
| Uridine | 5'-uridylic acid | 1.30 |
| Cytidine | 5'-cytidylic acid | 0.98 |

EXAMPLE 3
Production of 5'-Inosinic acid from Various Phosphate Compounds as Phosphate Group Donors by Acid Phosphatase Sample Derived from *Morganella morganii*

Inosine (2 g/dl) and sodium tripolyphosphate, sodium polyphosphate (trade name: Polygon P, produced by Chiyoda Chemical), disodium phenylphosphate, or disodium carbamyl phosphate (10 g/dl) as a phosphate group donor were dissolved in sodium acetate buffer (pH 4.0), to which the enzyme sample prepared in Example 1 was added so that its concentration was 50 units/dl. The reaction mixture was incubated at 30° C. for 3 hours while maintaining pH at 4.0. The amount of 5'-inosinic acid produced by the reaction is shown in Table 3.

5'-Inosinic acid was efficiently produced and accumulated by using any of the phosphate group donors. However, the accumulated amount of 5'-inosinic acid was the highest when sodium polyphosphate was used as the phosphate group donor.

TABLE 3

| Phosphate group donor | Produced 5'-inosinic acid (g/dl) |
| --- | --- |
| Sodium tripolyphosphate | 2.10 |
| Sodium polyphosphate | 2.72 |
| Disodium phenylphosphate | 2.33 |
| Disodium carbamyl phosphate | 2.54 |

EXAMPLE 4
Purification and Characterization of Acid Phosphatase Derived from *Escherichia blattae*

A nutrient medium (pH 7.0, 50 ml) containing 1 g/dl of peptone, 0.5 g/dl of yeast extract, and 1 g/dl of sodium chloride was poured into Sakaguchi flasks (500 ml), which was sterilized at 120° C. for 20 minutes. A slant culture of *Escherichia blattae* JCM 1650 was inoculated to each of the flasks once with a platinum loop, which was cultivated at 30° C. for 16 hours with shaking. Microbial cells were harvested from a culture by centrifugation. The microbial cells (about 3,300 g) were suspended in 100 mM potassium phosphate buffer (1 L, pH 7.0). A ultrasonic treatment was performed at 4° C. for 20 minutes to disrupt the microbial cells. The treated suspension was centrifuged to remove its insoluble fraction. Thus a cell-free extract was prepared.

Ammonium sulfate was added to the cell-free extract so that 30% saturation was achieved. Appeared precipitate was removed by centrifugation, and then ammonium sulfate was further added to supernatant so that 60% saturation was achieved. Appeared precipitate was recovered by centrifugation, and it was dissolved in 100 mM potassium phosphate buffer.

This crude enzyme solution was dialyzed four times against 5 L of 100 mM potassium phosphate buffer (pH 7.0), and then it was applied to a DEAE-Toyopeal 650M column ($\phi 6.2 \times 35$ cm) equilibrated with 20 mM potassium phosphate buffer (pH 7.0), followed by washing with 20 mM potassium phosphate buffer (pH 7.0). The transphosphorylation activity was found in a fraction which passed through the column, and thus the fraction was collected.

The active fraction was added with ammonium sulfate so that 35% saturation was achieved, which was applied to a Butyl-Toyopeal column ($\phi 5.0 \times 22.5$ cm) equilibrated with 20 mM potassium phosphate buffer (pH 7.0) containing ammonium sulfate at 35% saturation. Elution was performed by using a linear concentration gradient from 35% saturation to 20% saturation in potassium phosphate buffer (pH 7.0).

Active fractions were collected and dialyzed against 1 L of 100 mM potassium phosphate buffer (pH 7.0), followed by being applied to a hydroxyapatite column ($\phi 3.0 \times 7.0$ cm) equilibrated with 100 mM potassium phosphate buffer (pH 7.0). Elution was performed by using a linear concentration gradient from 50 mM to 100 mM of potassium phosphate buffer (pH 7.0), and active fractions were collected.

This enzyme solution was dialyzed against 1 L of 10 mM potassium phosphate buffer (pH 6.0), followed by being applied to a CM-Toyopearl column ($\phi 2.0 \times 14.0$ cm) equilibrated with 10 mM potassium phosphate buffer (pH 6.0). Elution was performed by using a linear concentration gradient in potassium phosphate buffer (pH 6.0) containing from 0 mM to 300 mM potassium chloride. Active fractions eluted from the column were collected.

In accordance with the procedure as described above, the enzyme exhibiting the transphosphorylation activity was purified from the cell-free extract consequently about 600-fold at a recovery ratio of about 16%. The specific activity and the recovery ratio in this purification process are shown in Table 4. This enzyme sample was homogeneous on SDS-polyacrylamide gel electrophoresis.

TABLE 4

| Step | Total activity (unit) | Total protein (mg) | Specific activity (unit/mg) | Recovery ratio (%) |
| --- | --- | --- | --- | --- |
| 1. Cell-free extract | 365 | 160,650 | 0.002 | 100 |
| 2. Ammonium sulfate fractionation (30 to 60 %) | 340 | 138,895 | 0.002 | 93 |
| 3. DEAE-Toyopearl | 318 | 30,440 | 0.010 | 87 |
| 4. Butyl-Toyopearl | 232 | 661 | 0.347 | 63 |
| 5. Hydroxyapatite | 96 | 96 | 1.000 | 26 |
| 6. CM-Toyopearl | 59 | 43 | 1.365 | 16 |

The purified enzyme had the following properties.

(1) Action: Phosphate group is transferred from a phosphate group donor such as polyphosphoric acid to nucleoside, and nucleoside-5'-phosphate ester is produced. Reversely, this enzyme also exhibits an activity to hydrolyze phosphate ester.

(2) Substrate specificity: Those which serve as the phosphate group donor in the transphosphorylation reaction include, for example, pyrophosphoric acid, tripolyphosphoric acid, trimetaphosphoric acid, tetrametaphosphoric acid, hexametaphosphoric acid, disodium phenylphosphate, dipotassium phenylphosphate, O,O-diphenylphosphoric acid anhydride, disodium carbamyl phosphate, dipotassium carbamyl phosphate, diammonium carbamyl phosphate, and dilithium carbamyl phosphate. Those which serve as the phosphate group acceptor include, for example, purine riboside, inosine, guanosine, adenosine, xanthosine, uridine, and cytidine. On the other hand, those which undergo the action in the phosphate ester hydrolytic reaction include, for example, inorganic phosphoric acid such as pyrophosphoric acid, tripolyphosphoric acid, trimetaphosphoric acid, tetrametaphosphoric acid, hexametaphosphoric acid; phosphate ester such as disodium phenylphosphate, dipotassium phenylphosphate, O,O-diphenylphosphoric acid anhydride, disodium carbamyl phosphate, dipotassium carbamyl phosphate, diammonium carbamyl phosphate, and dilithium carbamyl phosphate; and 5'-nucleotide such as 5'-purine ribotide, 5'-inosinic acid, 5'-guanylic acid, 5'-adenylic acid, 5'-xanthylic acid, 5'-uridylic acid, and 5'-cytidylic acid.

(3) Optimum pH: 5.2 (transphosphorylation reaction), 6.5 (phosphate ester hydrolytic reaction).

(4) pH stability: pH 3.5 to 12.0 (treatment at 30° C. for 60 minutes).

(5) Optimum temperature: about 35° C.

(6) Temperature stability: stable up to 40° C. (treatment at pH 7.0 for 30 minutes).

(7) Effect of the addition of metal ion and inhibitor: This enzyme exhibits no activation phenomenon relevant to its activity by addition of any metal ion The activity is inhibited by $Fe^{2+}$, $Ag^{2+}$, $Pb^{2+}$, $Hg^{2+}$, and $Cu^{2+}$. The activity is also inhibited by iodoacetic acid.

(8) Molecular weight: A calculated molecular weight is about 188,000 in accordance with high-performance liquid chromatography (TSKgel G-3000SW, produced by Toyo Soda).

(9) Subunit molecular weight: A calculated subunit molecular weight is about 24,500 in accordance with SDS-polyacrylamide gel electrophoresis.

This enzyme also exhibits not only the activity to transfer phosphate group to nucleoside, but also the activity to reversely hydrolyze phosphate ester, in the same manner as the enzyme purified from the cell-free extract of *Morganella morganii* NCIMB 10466. Moreover, this enzyme exhibits the phosphate ester hydrolytic activity (phosphomonoesterase activity) which is higher than the transphosphorylation activity by not less than 30 times. Accordingly, it has been clarified that this enzyme is an acid phosphatase.

Figure 2:
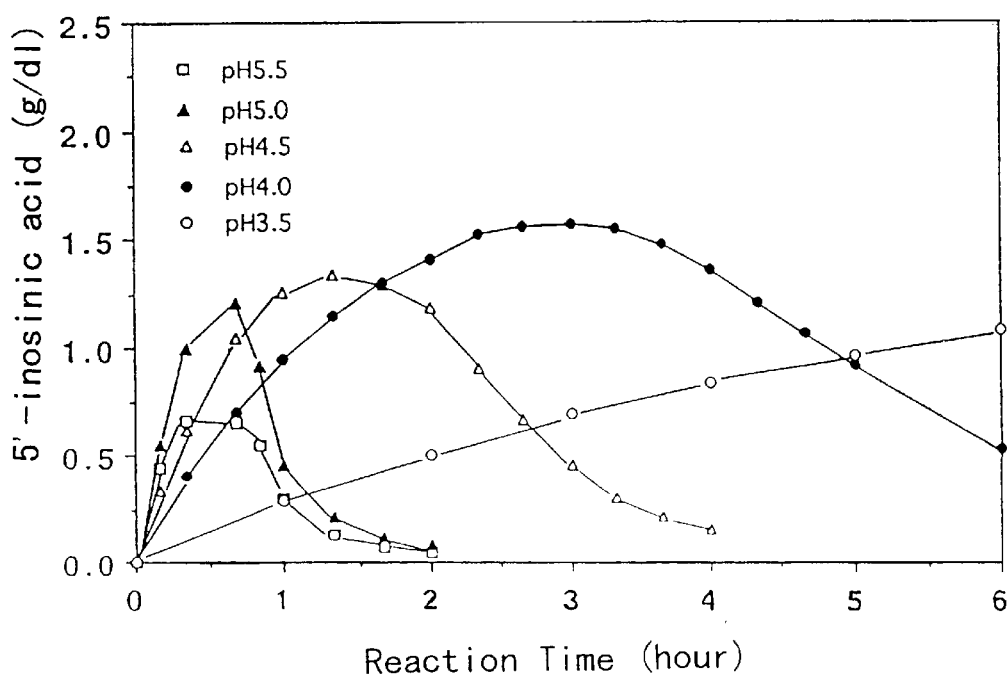
FIG. 2 illustrates a relationship between reaction pH and produced amount of 5'-inosinic acid in a reaction performed by using an enzyme derived from *Escherichia blattae*.

Sodium pyrophosphate (15 g/dl) and inosine (3 g/dl) were dissolved in sodium acetate buffers each having pH of 5.5, 5.0, 4.5, 4.0, and 3.5, to which the enzyme sample described above was added so that a concentration of 50 units/dl was obtained. The reaction mixture was incubated at 30° C. for 6 hours while maintaining each pH, and the amount of produced 5'-inosinic acid was measured along with passage of time. Produced inosinic acid contained only 5'-inosinic acid. By-production of 2'-inosinic acid and 3'-inosinic acid was not observed at all. A result is shown in FIG. 2. The velocity of 5'-inosinic acid production was maximum at pH 5.0. However, the maximum accumulated amount of 5'-inosinic acid was higher at lower pH. The reaction condition at pH 4.0 was most efficient for production of 5'-inosinic acid. 5'-Inosinic acid was produced and accumulated in an amount of 1.56 g/dl by performing the reaction at 30° C. at pH 4.0 for 3 hours.

EXAMPLE 5
Phosphorylation Reaction of Various Nucleosides by Acid Phosphatase Sample Derived from *Escherichia blattae*

Sodium pyrophosphate (15 g/dl) and inosine, guanosine, uridine, or cytidine (3 g/dl) were dissolved in sodium acetate buffer (pH 4.0), to which the enzyme sample prepared in Example 4 was added so that its concentration was 50 units/dl. The reaction mixture was incubated at 35° C. for 3 hours while maintaining pH at 4.0. The amount of produced nucleoside-5'-ester is shown in Table 5.

Produced nucleotide contained only nucleoside-5'-ester. By-production of nucleoside-2'-ester and nucleoside-3'-ester was not observed at all.

TABLE 5

| Nucleoside | Product | Produced amount (g/dl) |
|---|---|---|
| Inosine | 5'-inosinic acid | 1.56 |
| Guanosine | 5'-guanylic acid | 1.05 |
| Uridine | 5'-uridylic acid | 1.87 |
| Cytidine | 5'-cytidylic acid | 1.22 |

EXAMPLE 6
Production of 5'-Inosinic acid from Various Phosphate Compounds as Phosphate Group Donors by Acid Phosphatase Sample Derived from *Escherichia blattae*

Inosine (2 g/dl) and sodium tripolyphosphate, sodium polyphosphate (trade name: Polygon P, produced by Chiyoda Chemical), disodium phenylphosphate, or disodium carbamyl phosphate (10 g/dl) as a phosphate group donor were dissolved in sodium acetate buffer (pH 4.0), to which the enzyme sample prepared in Example 4 was added so that its concentration was 50 units/dl. The reaction miture was incubated at 35° C. for 3 hours while maintaining pH at 4.0. The amount of produced 5'-inosinic acid is shown in Table 6.

5'-Inosinic acid was efficiently produced and accumulated by using any of the phosphate group donors. However, the accumulated amount of 5'-inosinic acid was the highest when sodium polyphosphate was used as the phosphate group donor.

TABLE 6

| Phosphate group donor | Produced 5'-inosinic acid (g/dl) |
|---|---|
| Sodium tripolyphosphate | 1.20 |
| Sodium polyphosphate | 1.79 |
| Disodium phenylphosphate | 1.50 |
| Disodium carbamyl phosphate | 1.53 |

EXAMPLE 7
Isolation of Gene Coding for Acid Phosphatase from Chromosome of *Morganella morganii*

(1) Determination of N-terminal amino acid sequence

The acid phosphatase purified from the cell-free extract of *Morganella morganii* NCIMB 10466 in accordance with the method described in Example 1 was adsorbed to DITC membrane (produced by Milligen/Biosearch), and its N-terminal amino acid sequence was determined by using Prosequencer 6625 (produced by Milligen/Biosearch). An N-terminal amino acid sequence comprising 20 residues shown in SEQ ID NO: 1 in Sequence Listing was determined.

(2) Isolation of DNA fragment containing gene coding for acid phosphatase

Chromosomal DNA was extracted from cultivated microbial cells of *Morganella morganii* NCIMB 10466 in accordance with a method of Murray and Thomson (*Nucl. Acid Res.*, 4321, 8 (1980)). The chromosomal DNA was partially degraded with restriction enzyme Sau3AI. After that, DNA fragments of 3 to 6 kbp were fractionated by means of sucrose density gradient centrifugation. A plasmid vector pUC118 (produced by Takara Shuzo) was digested with restriction enzyme BamHI, which was ligated with the partially degraded chromosomal DNA fragments. DNA ligation was performed by using DNA ligation kit (produced by Takara Shuzo) in accordance with a designated method. After that, *Escherichia coli* JM109 (produced by Takara Shuzo) was transformed with an obtained DNA mixture in accordance with an ordinary method. Transformants were plated on an L agar medium containing 100 µg/ml of ampicillin, and they were grown to prepare a gene library.

A reaction solution containing 4 mM p-nitrophenylphosphoric acid and 100 mM MES/NaOH buffer (pH 6.5) was poured onto a surface of the agar medium on which the transformants had grown, and the temperature was kept at 30° C. for 15 minutes. Strains which had expressed the phosphatase activity liberated p-nitrophenol and exhibited a yellow color. Accordingly, transformants were selected by using this phenomenon as an index. As a result of screening for a gene expression library comprising about 20,000 strains of transformants, 30 strains of transformants which had expressed the phosphatase activity were obtained.

The transformants (30 strains), which had expressed the phosphatase activity, were subjected to single colony isolation. Single colonies were inoculated to an L-medium (2.5 ml) containing 100 µg/ml of ampicillin, and they were cultivated at 37° C. for 16 hours. Sodium acetate buffer (100 mM, pH 5.0, 50 µl) containing inosine (2 g/dl) and sodium pyrophosphate (10 g/dl) was added to microbial cells harvested from culture, and the reaction mixture was incubated at 30° C. for 16 hours. Production of 5'-inosinic acid was detected by HPLC analysis to select microbial strains having the transphosphorylation activity. As a result, we succeeded in obtaining 5 strains of transformants which exhibited the transphosphorylation activity and which were assumed to harbor a DNA fragment containing the objective acid phosphatase gene.

EXAMPLE 8
Determination of Nucleotide Sequence of Acid Phosphatase Gene Derived from *Morganella morganii* NCIMB 10466

Figure 3:
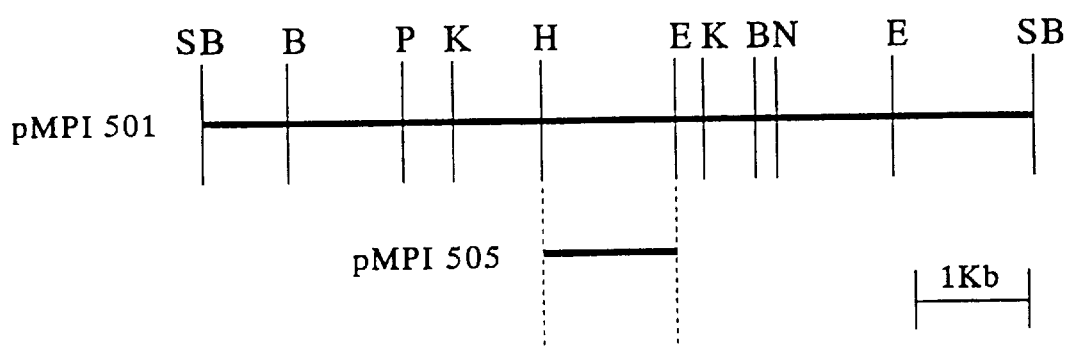
FIG. 3 illustrates a restriction enzyme map of a chromosomal DNA fragment of *Morganella morganii* containing a gene coding for an acid phosphatase.

The inserted DNA fragment was analyzed by preparing a plasmid in accordance with an alkaline lysis method (*Molecular Cloning* 2nd edition (J. Sambrook, E. F. Fritsch and T. Maniatis, Cold Spring Harbour Laboratory Press, pl. 25 (1989)) from one strain of the transformants which were assumed to harbor the DNA fragment containing the acid phosphatase gene derived from *Morganella morganii* NCIMB 10466 obtained in Example 7. This plasmid was designated as pMPI501. FIG. 3 shows a determined restriction enzyme map of the inserted DNA fragment.

The region of the acid phosphatase gene was further specified by subcloning. As a result, it was suggested that this acid phosphatase gene was contained in a fragment having a size of 1.2 Kbp excised by restriction enzymes HindIII and EcoRI. Thus in order to determine the nucleotide sequence, plasmid DNA was constructed in which the fragment of 1.2 kbp was ligated with pUC118 having been digested with HindIII and EcoRI. *Escherichia coli* JM109 (produced by Takara Shuzo) was transformed with this plasmid DNA designated as pMPI505 in accordance with an ordinary method, which was plated on an L agar medium containing 100 µg/ml of ampicillin to obtain a transformant.

The plasmid was extracted in accordance with the alkaline lysis method from the transformant of *Escherichia coli* JM109 (produced by Takara Shuzo) harboring pMPI505 to determine the nucleotide sequence. The nucleotide sequence was determined in accordance with a method of Sanger (*J. Mol. Biol.*, 143, 161 (1980)) by using Taq DyeDeoxy Terminator Cycle Sequencing Kit (produced by Applied Biochemical). A nucleotide sequence of a determined open reading frame is shown in SEQ ID NO: 2 in Sequence Listing. An amino acid sequence of the protein deduced from the nucleotide sequence is shown in SEQ ID NO: 3 in Sequence Listing. A partial sequence, which was completely coincident with the N-terminal amino acid sequence of the purified enzyme, was found in the amino acid sequence. The N-terminal of the purified enzyme starts from the 21th alanine residue of the sequence shown in SEQ ID NO: 3. Accordingly, it is assumed that the amino acid sequence shown in SEQ ID NO: 3 is that of a precursor protein, and that a peptide comprising a range from the 1st methionine residue to the 20th alanine residue is eliminated after translation. An amino acid sequence of a mature protein thus deduced is shown in SEQ ID NO: 4 in Sequence Listing. A molecular weight of the mature protein estimated from the amino acid sequence is calculated to be 24.9 kilodaltons, which is well coincident with the result of SDS-PAGE for the purified enzyme. According to the results described above, and because of the fact that the transformant harboring the plasmid containing this fragment exhibited the transphosphorylation activity, it was identified that this open reading frame was the region coding for the objective acid phosphatase.

The nucleotide sequence and the amino acid sequence were respectively compared with known sequences for homology. Data bases of EMBL and SWISS-PROT were used. As a result, it has been revealed that the nucleotide sequence shown in SEQ ID NO: 2 in Sequence Listing is coincident with a nucleotide sequence of a known acid phosphatase gene derived from *Morganella morganii* (Thaller, M. C. et al., *Microbiology*, 140, 1341 (1994)) except that 54th G is A, 72th G is A, 276th T is G, 378th T is C, 420th G is T, 525th C is G, 529th C is T, and 531th G is A in the latter, and that the amino acid sequence shown in SEQ ID NO: 4 in Sequence Listing is the same as that of the acid phosphatase gene derived from *Morganella morganii*. Namely, the gene, which codes for the protein comprising the amino acid sequence shown in SEQ ID NO: 4 in Sequence Listing, is the acid phosphatase gene of *Morganella morganii* NCIMB 10466.

A precursor protein comprises 249 amino acids, and a molecular weight of the protein deduced from its sequence is 27.0 kilodaltons.

The strain of *Escherichia coli* JM109 transformed by a plasmid pMPI505, has been designated as AJ13143, which has been internationally deposited on Feb. 23, 1996 in National Institute of Bioscience and Human Technology of Agency of Industrial Science and Technology (postal code: 305, 1–3, Higashi 1-chome, Tsukuba-shi, Ibaraki-ken, Japan) under the provision of the Budapest Treaty, and awarded a deposition number of FERM BP-5422.

EXAMPLE 9
Amplification of Activity by Expressing Gene of Acid Phosphatase Derived from *Morganella morganii* NCIMB 10466

Escherichia coli JM109/pMPI505 constructed in Example 8 was inoculated to an L-medium (50 ml) containing 100 μg/ml of ampicillin and 1 mM of IPTG, and it was cultivated at 37° C. for 16 hours. Microbial cells were harvested from its culture by centrifugation, and they were washed once with physiological saline. The microbial cells were suspended in 100 mM potassium phosphate buffer (5 ml, pH 7.2), and they were disrupted by means of a ultrasonic treatment performed at 4° C. for 20 minutes. The treated solution was centrifuged to remove an insoluble fraction, and thus a cell-free extract was prepared.

The transphosphorylation activity of the obtained cell-free extract was measured while using controls of cell-free extracts prepared from the wild type strain of *Morganella morganii* and *Escherichia coli* JM109 transformed with the plasmid pUC118 in the same manner as described above. A result is shown in Table 7. The transphosphorylation activity was not detected in *Escherichia coli* JM109/pUC118. The transphosphorylation activity was also low in the wild type strain of *Morganella morganii*. On the other hand, *Escherichia coli* JM109/pMPI505 exhibited a high transphosphorylation activity which was 150 times as high as that of the wild type strain of *Morganella morganii* in sepcific activity. According to the result, it has been demonstrated that the introduced DNA fragment allows *Escherichia coli* to express the acid phosphatase at a high level.

TABLE 7

| Microbial strain | Transphosphrylation Activity (units/mg) |
| --- | --- |
| *Morganella morganii* NCIMB 10466 | 0.008 |
| *Escherichia coli* JM109/pUC118 | not detected |
| *Escherichia coli* JM109/pMPI505 | 1.250 |

EXAMPLE 10
Production of 5'-Inosinic Acid from Inosine by Using Strain Harboring Acid Phosphatase Gene Derived from *Morganella morganii* NCIMB 10466

Figure 4:
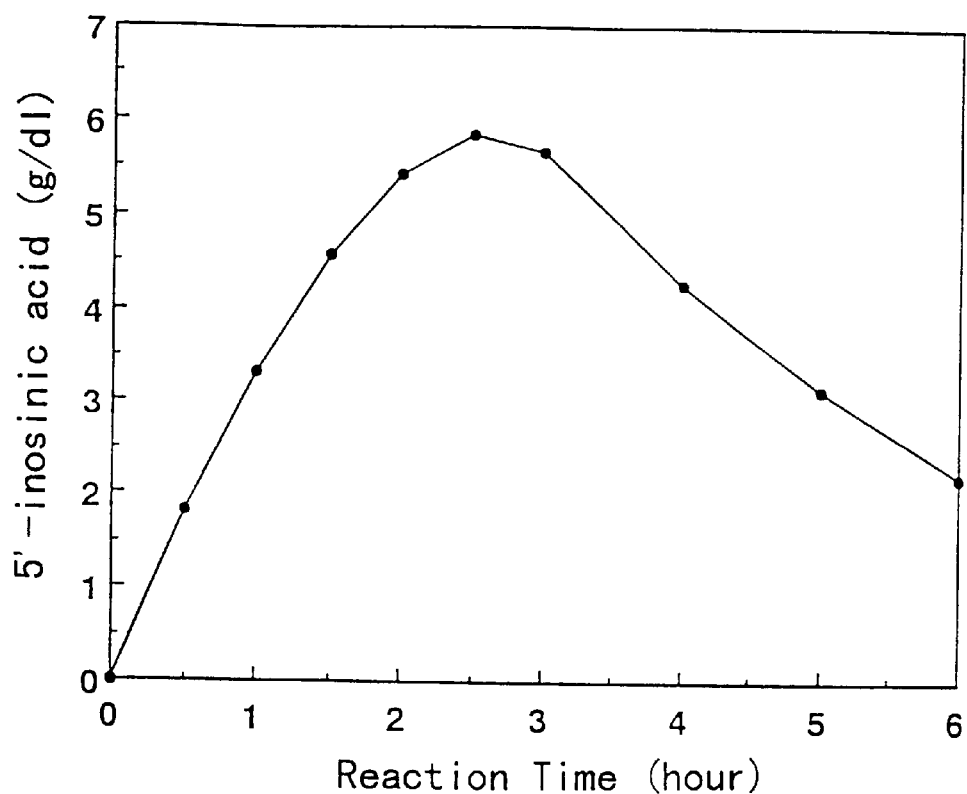
FIG. 4 illustrates produced amount of 5'-inosinic acid in a reaction performed by using a strain harboring phosphatase gene derived from *Morganella morganii*.

Sodium pyrophosphate (12 g/dl) and inosine (6 g/dl) were dissolved in 100 mM sodium acetate buffer (pH 4.0), to which the microbial cells of *Escherichia coli* JM109/pMPI505 described above were added to give a cell concentration of 100 mg/dl as converted into a dry weight of the microbial cells. The reaction mixture was incubated at 30° C. for 6 hours while maintaining pH at 4.0, and the amount of produced 5'-inosinic acid was measured along with passage of time. Produced inosinic acid contained only 5'-inosinic acid. By-production of 2'-inosinic acid and 3'-inosinic acid was not observed at all. A result is shown in FIG. 4. The stain harboring the acid phosphatase gene expressed a considerable amount of the acid phosphatase, and 5'-inosinic acid was produced and accumulated extremely efficiently in a short period of time in the reaction to produce 5'-inosinic acid from pyrophosphate and inosine by using this microorganism. However, when the reaction time is prolonged, it was observed that the produced and accumulated 5'-inosinic acid was decreased due to degradation.

EXAMPLE 11
Preparation of Phosphomonoesterase activity-Lowered Type Acid Phosphatase Gene As described in Examples 9 and 10, the strain harboring the acid phosphatase gene expresses a considerable amount of the acid phosphatase, and 5'-inosinic acid is produced and accumulated extremely efficiently in a short period of time in the reaction to produce 5'-inosinic acid from pyrophosphate and inosine by using this microorganism. However, it has been revealed that the accumulated amount of 5'-inosinic acid does not exceed a certain degree because produced 5'-inosinic acid undergoes degradation by the phosphomonoesterase activity possessed by the acid phosphatase itself. Thus the enzyme was improved by introducing mutation into the acid phosphatase gene derived from *Morganella morganii* NCIMB 10466 cloned in Example 7, in accordance with the site-directed mutagenesis method by using PCR.

Oligonucleotides MUT500, MUT510, and MUT520 having sequences shown in SEQ ID NOs: 5, 6, and 7 in Sequence Listing were synthesized respectively in accordance with the phosphoamidite method by using a DNA synthesizer (Model 394 produced by Applied Biosystems).

The plasmid pMPI505 (1 ng) as a template prepared in Example 8, M13 primer RV (produced by Takara Shuzo) and MUT510 oligonucleotide (each 2.5 μmol) as primers, and Taq DNA polymerase (2.5 units, produced by Takara Shuzo) were added to 100 mM Tris-HCl buffer (pH 8.3, 100 μl) containing dATP, dCTP, dGTP, dTTP (each 200 μM), potassium chloride (50 mM), and magnesium chloride (1.5 mM) to perform a PCR reaction in which a cycle comprising periods of 30 seconds at 94° C., 2 minutes at 55° C., and 3 minutes at 72° C. was repeated 25 times. The PCR reaction was performed by using Thermal Cycler PJ2000 type (produced by Takara Shuzo). Also, a PCR reaction was performed in the same manner as described above by using plasmid DNA pMPI505 (1 ng) as a temperate, and M13 primer M4 (produced by Takara Shuzo) and MUT500 oligonucleotide (each 2.5 μmol) as primers. Each of the reaction products was purified by gel filtration to remove the primers by using Microspin column S-400 (produced by Pharmacia).

Each of the PCR reaction products (1 μl) was added to 100 mM Tris-HCl buffer (pH 8.3, 95 μl) containing dATP, dCTP, dGTP, dTTP (each 200 μM), potassium chloride (50 mM), and magnesium chloride (1.5 mM), and it was heated at 94° C. for 10 minutes, followed by cooling to 37° C. over 60 minutes. After that, the temperature was kept at 37° C. for 15 minutes to form a heteroduplex. Taq DNA polymerase (2.5 units) was added thereto to perform a reaction at 72° C. for 3 minutes so that the heteroduplex was completed. After that, M13 primer RV and M13 primer M4 (each 2.5 μmol) were added to this reaction solution to perform a PCR reaction in which a cycle comprising periods of 30 seconds at 94° C., 2 minutes at 55° C., and 3 minutes at 72° C. was repeated 10 times.

A product of the second PCR reaction was digested with HindIII and EcoRI followed by phenol/chloroform extraction and ethanol precipitation. This DNA fragment was ligated with pUC118 having been digested with HindIII and EcoRI. *Escherichia coli* JM109 (produced by Takara Shuzo) was transformed with obtained plasmid DNA in accordance with an ordinary method, which was plated on an L agar medium containing 100 μg/ml of ampicillin to obtain a transformant. The plasmid was extracted from the transformant in accordance with the alkaline lysis method to determine its nucleotide sequence, confirming that the objective nucleotide was substituted. The nucleotide sequence was determined in accordance with a method of Sanger (*J. Mol. Biol.*, 143, 161 (1980)) by using Taq DyeDeoxy Terminator Cycle Sequencing Kit (produced by Applied Biochemical). Thus a mutant gene coding for a mutant phosphatase was prepared in which the 72th glycine residue (GGT) of the mature protein was substituted with an aspartic acid residue (G*AT). The plasmid containing this mutant gene was designated as pMPI510.

Further, a mutant gene coding for a mutant phosphatase was prepared in which the 151th isoleucine residue (ATC) of the mature protein was substituted with a threonine residue (A*CC), in accordance with the same procedure as described above by using pMPI505 as a template, and MUT500 and MUT520 oligonucleotides as primers. The plasmid containing this mutant gene was designated as pMPI520. Moreover, a mutant gene coding for a mutant phosphatase was prepared in which the 72th glycine residue (GGT) of the mature protein was substituted with an aspartic acid residue (G*AT), and the 151th isoleucine residue (ATC) of the mature protein was substituted with a threonine residue (A*CC), in accordance with the same procedure as described above by using pMPI510 as a template, and MUT500 and MUT520 oligonucleotides as primers. The plasmid containing this mutant gene was designated as pMPI530.

*Escherichia coli* JM109/pMPI510, *Escherichia coli* JM109/pMPI520, and *Escherichia coli* JM109/pMPI530 into which the plasmids containing the respective mutant acid phosphatase genes had been introduced, and *Escherichia coli* JM109/pMPI505 into which the plasmid containing the wild type acid phosphatase gene had been introduced were inoculated to an L medium (50 ml) containing 100 µg/ml of ampicillin and 1 mM of IPTG, and they were cultivated at 37° C. for 16 hours. Microbial cells were harvested from their culture, and they were washed once with physiological saline. The microbial cells were suspended in 100 mM potassium phosphate buffer (5 ml, pH 7.0), and were disrupted by means of a ultrasonic treatment performed at 4° C. for 20 minutes. The treated solutions were centrifuged to remove insoluble fractions, and thus cell-free extracts were prepared. Phosphomonoesterase activities and transphosphorylation acitivities of the obtained cell-free extracts were measured at pH 4.0, and they were compared with an activity of the wild strain.

Table 8 shows the result of mesurement of phosphomonoesterase activities and transphosphorylation acitivities of wild type acid phosphatase and mutant acid phosphatases. It shows that both of phosphomonoesterase activities and transphosphorylation acitivities of mutants acid phosphatases are lowered as compared with wild type acid phosphatase, and that degrees of decrease of phosphomonoesterase activities are larger than that of transphosphorylation activity, with the result that a ratio of phosphomonoesterase activity to transphosphorylation activity of the mutant acid phosphatase is lowered in comparison with the wild type acid phosphatase.

TABLE 8

| Plasmid | Phosphomonoesterase activity (units/mg) | Transphosphorylation activity (units/mg) | Ratio[1] (Relative value) |
| --- | --- | --- | --- |
| pMP1505 | 5.91 | 0.625 | 9.45 (100) |
| pMPI510 | 0.59 | 0.090 | 6.55 ( 69) |
| pMPI520 | 2.24 | 0.583 | 3.84 ( 40) |
| PMPI530 | 1.07 | 0.318 | 3.36 ( 35) |

[1]Ratio of phosphomonoesterase activities to the activities to produce nucleoside-5'-phosphate ester EXAMPLE 12
Production of 5'-Inosinic Acid from Inosine by Using The Strains Horboring A Gene Encoding The Acid Phosphatase with Lowered Phosphomonoesterase Activity

*Escherichia coli* JM109/pMPI510, *Escherichia coli* JM109/pMPI520, and *Escherichia coli* JM109/pMPI530 into which the plasmids containing the mutant acid phosphatase genes had been introduced, and *Escherichia coli* JM109/pMPI505 into which the plasmid containing the wild type acid phosphatase gene had been introduced were inoculated to an L medium (50 ml) containing 100 µg/ml of ampicillin and 1 mM of IPTG, and they were cultivated at 37° C. for 16 hours.

Sodium pyrophosphate (12 g/dl) and inosine (6 g/dl) were dissolved in 100 mM sodium acetate buffer (pH 4.0), to which microbial cells of each of the strains of *Escherichia coli* obtained by the cultivation described above were added to give a cell concentration of 100 mg/dl as converted into a dry weight of the microbial cells. The reaction mixture was incubated at 30° C. for 22 hours while maintaining pH at 4.0, and the amount of produced 5'-inosinic acid was measured along with passage of time. A result is shown in FIG. 5.

Figure 5:
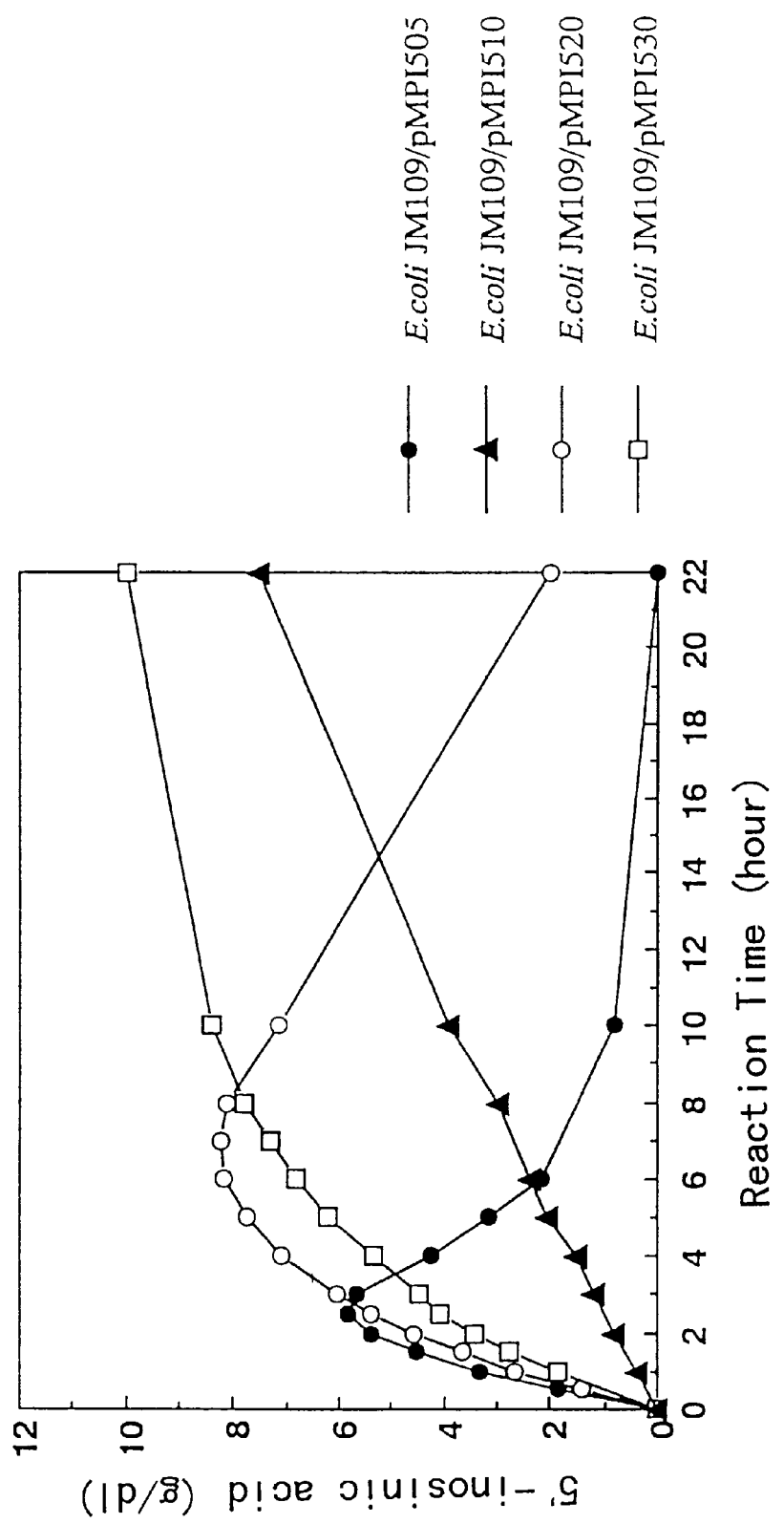
FIG. 5 illustrates produced amount of 5'-inosinic acid in reactions performed by using a strain horboring the wild type acid phosphatase gene and a strain horboring the mutant acid phosphatase gene derived from *Morganella morganii* respectively.

In FIG. 5, the axis of ordinate indicates the concentration of 5'-inosinic acid (mg/dl), and the axis of abscissa indicates the reaction time (h). Progress of the reaction is indicated by solid circles for *Escherichia coli* JM109/pMPI505, solid triangles for *Escherichia coli* JM109/pMPI510, blanked circles for *Escherichia coli* JM109/pMPI520, and blanked squares for *Escherichia coli* JM109/pMPI530, as measured by using the microbial cells of the respective strains.

The velocity of degradation of produced 5'-inosinic acid was decreased in the reaction to produce 5'-inosinic acid from inosine by using the strains harboring a gene encoding the acid phosphatase with lowered phosphomonoesterase activity. As a result, the yield and the accumulated amount of 5'-inosinic acid were increased. The highest accumulation of 5'-inosinic acid was exhibited by *Escherichia coli* JM109/pMPI530 as the strain harboring the mutant acid phosphatase gene in which the 72th glycine residue and the 151th isoleucine residue were substituted with the aspartic acid residue and the threonine residue respectively.

EXAMPLE 13
Production of Various Nucleoside-5'-Phosphate Esters by Using The Strains Horboring A Gene Encoding The Acid Phosphatase with Lowered Phosphomonoesterase Activity

*Escherichia coli* JM109/pMPI530 into which the plasmid containing the mutant acid phosphatase gene had been introduced was inoculated to an L medium (50 ml) containing 100 µg/ml of ampicillin and 1 mM of IPTG, and it was cultivated at 37° C. for 16 hours.

Sodium pyrophosphate (12 g/dl), and inosine, guanosine, uridine, or cytidine (6 g/dl) as a phosphate group acceptor were dissolved in 100 mM sodium acetate buffer (pH 4.0), to which the microbial cells described above were added to give a cell concentration of 100 mg/dl as converted into a dry weight of the cells. The reaction mixture was incubated at 30° C. for 22 hours while maintaining pH at 4.0. Amounts of produced nucleoside-5'-phosphate esters are shown in Table 9. Produced nucleotide contained only nucleoside-5'-phosphate ester. By-production of nucleoside-2'-phosphate ester and nucleoside-3'-phosphate ester was not observed at all.

TABLE 9

| Nucleoside | Product | Produced amount (g/dl) |
| --- | --- | --- |
| Inosine | 5'-inosinic acid | 10.01 |
| Guanosine | 5'-guanylic acid | 6.72 |

TABLE 9-continued

| Nucleoside | Product | Produced amount (g/dl) |
|---|---|---|
| Uridine | 5'-uridylic acid | 11.90 |
| Cytidine | 5'-cytidylic acid | 7.82 |

EXAMPLE 14
Production of 5'-Inosinic Acid from Various Phosphate Compounds as Phosphate Group Donors by Using The Strains Horboring A Gene Encoding The Acid Phosphatase with Lowered Phosphomonoesterase Activity Escherichia coli JM109/pMPI530 into which the plasmid containing the mutant acid phosphatase gene had been introduced was inoculated to an L medium (50 ml) containing 100 µg/ml of ampicillin and 1 mM of IPTG, and it was cultivated at 37° C. for 16 hours.

Inosine (6 g/dl) and sodium tripolyphosphate, sodium polyphosphate (trade name: Polygon P, produced by Chiyoda Chemical), disodium phenylphosphate, or disodium carbamyl phosphate (10 g/dl) as a phosphate group donor were dissolved in sodium acetate buffer (pH 4.5), to which the microbial cells described above were added to give a cell concentration of 100 mg/dl as converted into a dry weight of the microbial cells. The reaction mixture was incubated at 30° C. for 22 hours while maintaining pH at 4.0. The amount of produced 5'-inosinic acid is shown in Table 10. 5'-Inosinic acid was efficiently produced and accumulated by using any of the phosphate group donors. However, the accumulated amount of 5'-inosinic acid was the highest when polyphosphoric acid was used as the phosphate group donor.

TABLE 10

| Phosphate group donor | Produced 5'-inosinic acid (g/dl) |
|---|---|
| Sodium tripolyphosphate | 8.93 |
| Sodium polyphosphate | 11.45 |
| Disodium phenylphosphate | 9.62 |
| Disodium carbamyl phosphate | 9.89 |

EXAMPLE 15
Isolation of Gene Coding for Acid Phosphatase from Chromosome of Escherichia blattae
(1) Determination of N-terminal amino acid sequence The acid phosphatase purified from the cell-free extract of Escherichia blattae JCM 1650 was adsorbed to DITC membrane (produced by Milligen/Biosearch), and its N-terminal amino acid sequence was determined by using Prosequencer 6625 (produced by Milligen/Biosearch). An N-terminal amino acid sequence comprising 15 residues shown in SEQ ID NO: 8 in Sequence Listing was determined.
(2) Isolation of DNA fragment containing gene coding for acid phosphatase Chromosomal DNA was extracted from cultivated cells of Escherichia blattae JCM 1650 in accordance with a method of Murray and Thomson (Nucl. Acid Res., 4321, 8 (1980)). The chromosomal DNA was partially degraded with Sau3AI. After that, DNA fragments of 3 to 6 kbp were fractionated by means of sucrose density gradient centrifugation. A plasmid vector pUC118 (produced by Takara Shuzo) was digested with BamHI, which was ligated with the partially degraded chromosomal DNA fragments. DNA ligation was performed by using DNA ligation kit (produced by Takara Shuzo) in accordance with a designated method. After that, Escherichia coli JM109 (produced by Takara Shuzo) was transformed with an obtained DNA mixture in accordance with an ordinary method. Transformants were plated on an L agar medium containing 100 µg/ml of ampicillin, and they were grown to prepare a gene library.

A reaction solution containing 4 mM p-nitrophenylphosphoric acid and 100 mM MES/NaOH buffer (pH 6.5) was poured onto a surface of the agar medium on which the transformants had grown, and the temperature was kept at 30° C. for 15 minutes. Strains which had expressed the phosphatase activity liberated p-nitrophenol and exhibited a yellow color. Accordingly, transformants were selected by using this phenomenon as an index. As a result of screening for a chromosomal gene expression library comprising about 8,000 strains of transformants, 14 strains of transformants which had expressed the phosphatase activity were obtained.

The transformants (14 strains), which had expressed the phosphatase activity, were subjected to single colony isolation. Single colonies were inoculated to an L-medium (2.5 ml) containing 100 µg/ml of ampicillin, and they were cultivated at 37° C. for 16 hours. Sodium acetate buffer (100 mM, pH 5.0, 50 µl) containing inosine (2 g/dl) and sodium pyrophosphate (10 g/dl) was added to microbial cells harvested from culture liquids to perform the reaction at 30° C. for 16 hours. Production of 5'-inosinic acid was detected by HPLC analysis to select strains having the transphosphorylation activity. As a result, we succeeded in obtaining 3 strains of transformants which exhibited the transphosphorylation activity and which were assumed to harbor a DNA fragment containing the objective acid phosphatase gene.

EXAMPLE 16
Determination of Nucleotide Sequence of Acid Phosphatase Gene Derived from Escherichia blattae JCM 1650

The inserted DNA fragment was analyzed by extracting a plasmid in accordance with the alkaline lysis method from one strain of the transformants which were assumed to harbor the DNA fragment containing the acid phosphatase gene derived from Escherichia blattae JCM 1650 obtained in Example 15. This plasmid was designated as pEPI301. FIG. 6 shows a determined restriction enzyme map of the inserted DNA fragment.

The region of the acid phosphatase gene was further specified by subcloning. As a result, it was suggested that this acid phosphatase gene was included in a fragment having a size of 2.4 Kbp excised by restriction enzymes ClaI and BamHI. Thus in order to determine the nucleotide sequence, plasmid DNA was constructed in which the fragment was ligated with pBluescript KS(+) (produced by Stratagene) having been digested with ClaI and BamHI. Escherichia coli JM109 (produced by Takara Shuzo) was transformed with the plasmid DNA designated as pEPI305 in accordance with an ordinary method, which was plated on an L agar medium containing 100 µg/ml of ampicillin to obtain a transformant.

The plasmid was extracted in accordance with the alkaline lysis method from the transformant of Escherichia coli JM109 (produced by Takara Shuzo) harboring pEPI305 to determine the nucleotide sequence. A nucleotide sequence of a determined open reading frame is shown in SEQ ID NO: 9 in Sequence Listing. An amino acid sequence of the protein deduced from the nucleotide sequence is shown in SEQ ID NO: 10 in Sequence Listing. A partial sequence, which was completely coincident with the N-terminal amino acid sequence of the purified enzyme, was found in the amino acid sequence. The N-terminal of the purified enzyme starts from the 19th leucine residue of the sequence shown in SEQ ID NO: 10. Accordingly, it is assumed that the amino acid sequence shown in SEQ ID NO: 10 is that of a precursor protein and that a peptide comprising a range from the 1st methionine residue to the 18th alanine residue is eliminated after translation. An amino acid sequence of a mature protein thus deduced is shown in SEQ ID NO: 11 in Sequence Listing. Accordingly, an estimated molecular weight of the mature protein is calculated to be 25.1 kilodaltons, which is well coincident with the result of SDS-PAGE for the purified enzyme. According to the results described above, and because of the fact that the transformant harboring the plasmid containing this fragment exhibited the transphosphorylation activity, it was identified that this open reading frame was the region coding for the objective acid phosphatase.

Namely, the gene, which codes for the protein comprising the amino acid sequence shown in SEQ ID NO: 11 in Sequence Listing, is the acid phosphatase gene of *Escherichia blattae* JCM 1650.

The nucleotide sequence and the amino acid sequence were respectively compared with known sequences for homology. Data bases of EMBL and SWISS-PROT were used. As a result, it has been revealed that the protein shown in SEQ ID NO: 8 and DNA coding for it are novel. A precursor protein encoded by this gene comprises 249 amino acids, and a molecular weight of the protein deduced from its sequence is 27.0 kilodaltons.

The amino acid sequence was compared with known sequences respectively for homology. As a result, this protein exhibited a high degree of homology with the acid phosphatase of *Providencia stuartii* (77.1%) with the acid phosphatase of *Morganella morganii* in Example 8 (77.1%), and with acid phosphatase of *Salmonella typhimurium* (44.3%).

The strain of *Escherichia coli* JM109 transformed by a plasmid pEPI305, has been designated as AJ13144, which has been internationally deposited on Feb. 23, 1996 in National Institute of Bioscience and Human Technology of Agency of Industrial Science and Technology (postal code: 305, 1–3, Higashi 1-chome, Tsukuba-shi, Ibaraki-ken, Japan) under the provision of the Budapest Treaty, and awarded a deposition number of FERM BP-5423.

EXAMPLE 17
Amplification of Activity by Expressing Gene of Acid Phosphatase Derived from *Escherichia blattae* JCM 1650

*Escherichia coli* JM109/pEPI305 constructed in Example 16 was inoculated to an L medium (50 ml) containing 100 μg/ml of ampicillin and 1 mM of IPTG, and it was cultivated at 37° C. for 16 hours. Microbial cells were harvested from its culture by centrifugation, and they were washed once with physiological saline. The microbial cells were suspended in 100 mM potassium phosphate buffer (5 ml, pH 7.2), and were disrupted by means of a ultrasonic treatment performed at 4° C. for 20 minutes. The treated solution was centrifuged to remove an insoluble fraction, and thus a cell-free extract was prepared.

The transphosphorylation activity of the obtained cell-free extract was measured while using controls of cell-free extracts prepared from the wild type strain of *Escherichia blattae* and *Escherichia coli* JM109 transformed with the plasmid pBluescript KS(+) in the same manner as described above. A result is shown in Table 11. The transphosphorylation activity was not detected in *Escherichia coli* JM109/pBluescript KS(+). The transphosphorylation activity was also low in the wild type strain of *Escherichia blattae*. On the other hand, *Escherichia coli* JM109/pEPI305 exhibited a high transphosphorylation activity which was 120 times as high as that of the wild type strain of *Escherichia blattae* in sepcific activity. According to the result, it has been demonstrated that the introduced DNA fragment allows *Escherichia coli* to express the acid phosphatase at a high level.

TABLE 11

| Microbial strain | Transphosphorylation Activity (units/mg) |
|---|---|
| *Escherichia blattae* JCM 1650 | 0.002 |
| *Escherichia coli* JM109/pBluescript KS(+) | not detected |
| *Escherichia coli* JM109/pEPI305 | 0.264 |

EXAMPLE 18
Production of 5'-Inosinic Acid from Inosine by Using Strain Harboring Acid Phosphatase Gene Derived from *Escherichia blattae* JCM 1650

Sodium pyrophosphate (12 g/dl) and inosine (6 g/dl) were dissolved in 100 mM sodium acetate buffer (pH 4.0), to which the microbial cells of *Escherichia coli* JM109/pEPI305 described above were added to give a cell concentration of 200 mg/dl as converted into a dry weight of the microbial cells. The reaction mixture was incubated at 35° C. for 10 hours while maintaining pH at 4.0, and the amount of produced 5'-inosinic acid was measured along with passage of time. Produced inosinic acid contained only 5'-inosinic acid. By-production of 2'-inosinic acid and 3'-inosinic acid was not observed at all. A result is shown in FIG. 7. 5'-Inosinic acid was produced and accumulated extremely efficiently in a short period of time in the reaction to produce 5'-inosinic acid from pyrophosphate and inosine by using this microorganism.

EXAMPLE 19
Preparation of A Gene Encoding An Acid Phosphatase with lowered Phosphomonoesterase acitivity As described in Examples 17 and 18, the strain harboring the acid phosphatase gene derived from *Escherichia blattae* expresses a considerable amount of the acid phosphatase, and 5'-inosinic acid is produced and accumulated extremely efficiently in a short period of time in the reaction to produce 5'-inosinic acid from pyrophosphate and inosine by using this microorganism. However, it has been revealed that the accumulated amount of 5'-inosinic acid does not exceed a certain degree because produced 5'-inosinic acid undergoes degradation by the phosphomonoesterase activity possessed by the acid phosphatase itself. Thus the enzyme was intended to be improved by introducing mutation into the acid phosphatase gene derived from *Escherichia blattae* cloned in Example 15, in accordance with the site-directed mutagenesis method by using PCR.

Oligonucleotides MUT300, MUT310, and MUT320 shown in SEQ ID NOs: 12, 13, and 14 in Sequence Listing were synthesized respectively in accordance with the phosphoamidite method by using a DNA synthesizer (Model 394 produced by Applied Biosystems).

The plasmid pEPI305 (1 ng) as a template prepared in Example 16, M13 primer RV (produced by Takara Shuzo) and MUT310 oligonucleotide (each 2.5 μmol) as primers, and Taq DNA polymerase (2.5 units, produced by Takara Shuzo) were added to 100 mM Tris-HCl buffer (pH 8.3, 100 μl) containing dATP, dCTP, dGTP, dTTP (each 200 μM), potassium chloride (50 mM), and magnesium chloride (1.5 mM) to perform a PCR reaction in which a cycle comprising periods of 30 seconds at 94° C., 2 minutes at 55° C., and 3 minutes at 72° C. was repeated 25 times. The PCR reaction was performed by using Thermal Cycler PJ2000 type (produced by Takara Shuzo). Also, a PCR reaction was performed in the same manner as described above by using plasmid pEPI305 (1 ng) as a temperate, and M13 primer M3 (produced by Takara Shuzo) and MUT300 oligonucleotide (each 2.5 μmol) as primers. Each of the reaction solutions was purified by gel filtration to remove the primers by using Microspin column S-400 (produced by Pharmacia).

Each of the PCR reaction products (1 μl) was added to 100 mM Tris-HCl buffer (pH 8.3, 95 μl) containing dATP, dCTP, dGTP, dTTP (each 200 μM), potassium chloride (50 mM), and magnesium chloride (1.5 mM), and it was heated at 94° C. for 10 minutes, followed by cooling to 37° C. over 60 minutes. After that, the temperature was kept at 37° C. for 15 minutes to form a heteroduplex. Taq DNA polymerase (2.5 units) was added thereto to perform a reaction at 72° C. for 3 minutes so that the heteroduplex was completed. After that, M13 primer RV and M13 primer M3 (each 2.5 μmol) were added to this reaction solution to perform a PCR reaction in which a cycle comprising periods of 30 seconds at 94° C., 2 minutes at 55° C., and 3 minutes at 72° C. was repeated 10 times.

A product of the second PCR reaction was digested with ClaI and BamHI followed by phenol/chloroform extraction and ethanol precipitation. This DNA fragment was ligated with pBluescript KS(+) having been digested with ClaI and BamHI. *Escherichia coli* JM109 (produced by Takara Shuzo) was transformed with obtained plasmid DNA in accordance with an ordinary method, which was plated on an L agar medium containing 100 μg/ml of ampicillin to obtain a transformant.

The plasmid was extracted from the transformant in accordance with the alkaline lysis method to determine its nucleotide sequence, confirming that the objective nucleotide was substituted. Thus a mutant gene coding for a mutant phosphatase was prepared in which the 74th glycine residue (GGG) of the mature protein was substituted with an aspartic acid residue (G*A*T). The plasmid containing this mutant gene was designated as pEPI310.

A mutant gene coding for a mutant phosphatase was prepared in which the 153th isoleucine residue (ATC) of the mature protein was substituted with a threonine residue (A*CC), in accordance with the same procedure as described above by using pEPI305 as a template, and MUT300 and MUT320 oligonucleotides as primers. The plasmid containing this mutant gene was designated as pEPI320. Further, a mutant gene coding for a mutant phosphatase was prepared in which the 74th glycine residue (GGG) of the mature protein was substituted with an aspartic acid residue (G*A*T), and the 153th isoleucine residue (ATC) of the mature protein was substituted with a threonine residue (A*CC), in accordance with the same procedure as described above by using pEPI310 as a template, and MUT300 and MUT320 oligonucleotides as primers. The plasmid containing this mutant gene was designated as pEPI330.

*Escherichia coli* JM109/pEPI310, *Escherichia coli* JM109/pEPI320, and *Escherichia coli* JM109/pEPI330 into which the plasmids containing the respective mutant acid phosphatase genes had been introduced, and *Escherichia coli* JM109/pEPI305 into which the plasmid containing the wild type acid phosphatase gene had been introduced were inoculated to an L medium (50 ml) containing 100 μg/ml of ampicillin and 1 mM of IPTG, and they were cultivated at 37° C. for 16 hours. Microbial cells were harvested from their culture, and they were washed once with physiological saline. The microbial cells were suspended in 100 mM potassium phosphate buffer (5 ml, pH 7.0), and they were disrupted by means of a ultrasonic treatment performed at 4° C. for 20 minutes. The treated solutions were centrifuged to remove insoluble fractions, and thus cell-free extracts were prepared. Phosphomonoesterase activities and transphosphorylation acitivities of the obtained cell-free extracts were measured at pH 4.0, and they were compared with an activity of the wild strain.

Table 12 shows the result of measurement of phosphomonoesterase activities and transphosphorylation acitivities of wild type acid phosphatase and mutant acid phosphatases. It shows that both of phosphomonoesterase activities and transphosphorylation acitivities of mutants acid phosphatases are lowered as compared with wild type acid phosphatase, and that degrees of decrease of phosphomonoesterase activities are larger than that of transphosphorylation activities, with the result that a ratio of phosphomonoesterase activity to transphosphorylation activity of the mutant acid phosphatase is lowered in comparison with the wild type acid phosphatase.

TABLE 12

| Plasmid | Phosphomonoesterase activity (units/mg) | Transphosphorylation activity (units/mg) | Ratio[1] (Relative value) |
| --- | --- | --- | --- |
| pEPI305 | 2.38 | 0.132 | 18.03 (100) |
| pEPI310 | 0.26 | 0.019 | 13.68 ( 76) |
| pEPI320 | 0.88 | 0.123 | 7.15 ( 39) |
| pEPI330 | 0.42 | 0.070 | 6.00 ( 33) |

[1]Ratio of phosphomonoesterase activities to the activities to produde nucleoside-5'-phosphate ester

EXAMPLE 20

Production of 5'-Inosinic Acid from Inosine by Using The Strains Horboring A Gene Encoding The Acid Phosphatase with Lowered Phosphomonoesterase Activity

*Escherichia coli* JM109/pEPI310, *Escherichia coli* JM109/pEPI320, and *Escherichia coli* JM109/pEPI330 into which the plasmids containing the mutant acid phosphatase genes had been introduced, and *Escherichia coli* JM109/pEPI305 into which the plasmid containing the wild type acid phosphatase gene had been introduced were inoculated to an L medium (50 ml) containing 100 μg/ml of ampicillin and 1 mM of IPTG, and they were cultivated at 37° C. for 16 hours.

Sodium pyrophosphate (12 g/dl) and inosine (6 g/dl) were dissolved in sodium acetate buffer (pH 4.0), to which microbial cells of each of the strains of *Escherichia coli* obtained by the cultivation described above were added to give a cell concentration of 200 mg/dl as converted into a dry weight of the microbial cells. The reaction mixture was incubated at 35° C. for 32 hours while maintaining pH at 4.0, and the amount of produced 5'-inosinic acid was measured along with passage of time. A result is shown in FIG. 8.

Figure 8:
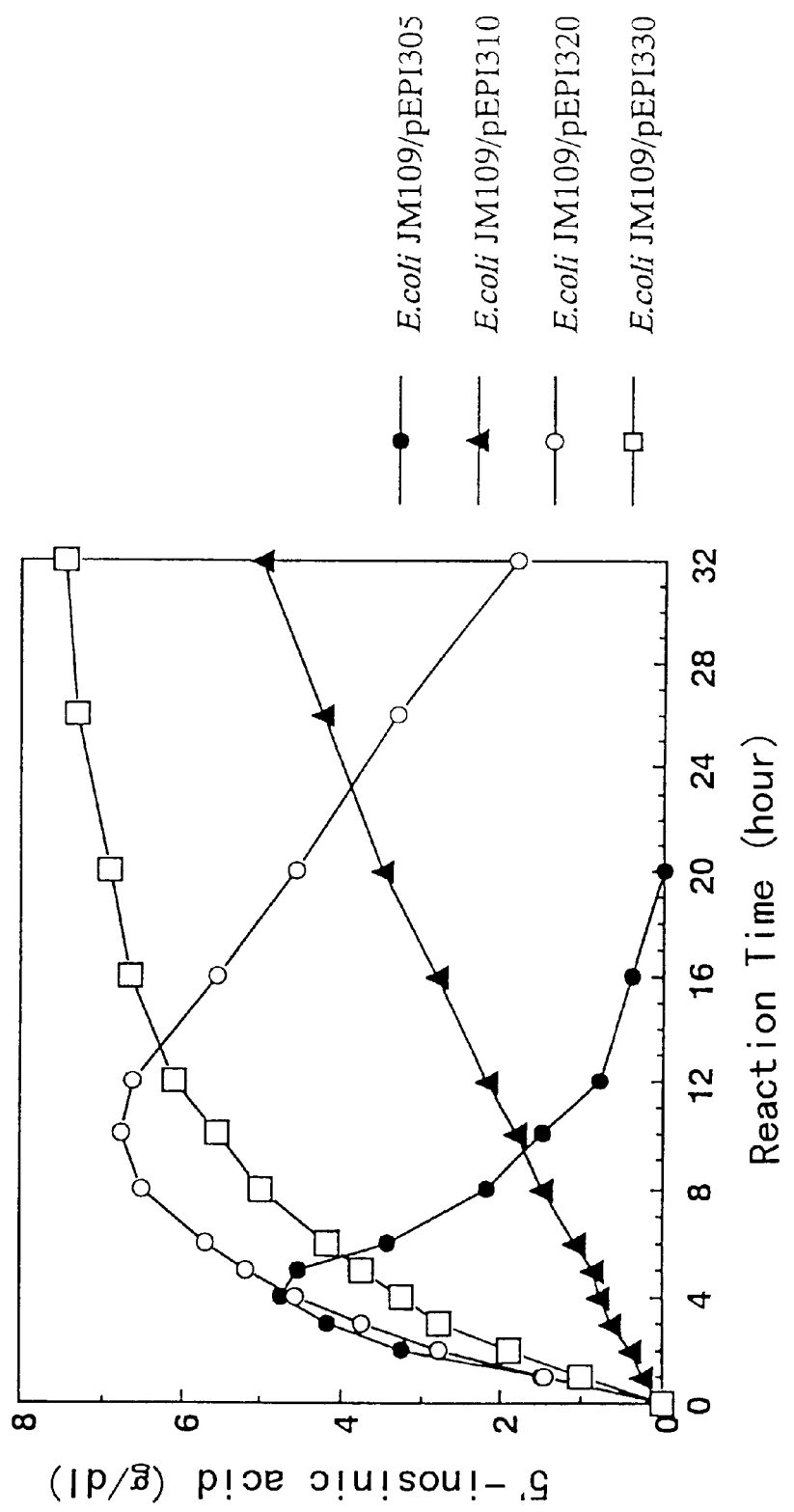
FIG. 8 illustrates produced amount of 5'-inosinic acid in reactions performed by using a strain harboring the wild type acid phosphatase gene and a strain harboring the mutant acid phosphatase gene derived from *Escherichia blattae* respectively.

In FIG. 8, the axis of ordinate indicates the concentration of 5'-inosinic acid (mg/dl), and the axis of abscissa indicates the reaction time (h). Progress of the reaction is indicated by solid circles for *Escherichia coli* JM109/pEPI305, solid triangles for *Escherichia coli* JM109/pEPI310, blanked circles for *Escherichia coli* JM109/pEPI320, and blanked squares for *Escherichia coli* JM109/pEPI330, as measured by using the cells of the respective strains.

The velocity of degradation of produced 5'-inosinic acid was decreased in the reaction to produce 5'-inosinic acid from inosine by using the stains harboring the acid phosphatase with lowered phosphomonoesterase activity. As a result, the yield and the accumulated amount of 5'-inosinic acid were increased. The highest accumulation of 5'-inosinic acid was exhibited by *Escherichia coli* JM109/pEPI330 as the strain harboring the mutant acid phosphatase gene in which the 74th glycine residue and the 153th isoleucine residue were substituted with the aspartic acid residue and the threonine residue respectively.

EXAMPLE 21
Production of Various Nucleoside-5'-Phosphate Esters by Using The Strains Horboring A Gene Encoding The Acid Phosphatase with Lowered Phosphomonoesterase Activity

*Escherichia coli* JM109/pEPI330 into which the plasmid containing the mutant acid phosphatase gene had been introduced was inoculated to an L medium (50 ml) containing 100 μg/ml of ampicillin and 1 mM of IPTG, and it was cultivated at 37° C. for 16 hours.

Sodium pyrophosphate (12 g/dl), and inosine, guanosine, uridine, or cytidine (6 g/dl) as a phosphate group acceptor were dissolved in 100 mM sodium acetate buffer (pH 4.0), to which the microbial cells described above were added to give a cell concentration of 200 mg/dl as converted into a dry weight of the cells. The reaction mixture was incubated at 35° C. for 32 hours while maintaining pH at 4.0. Amounts of produced nucleoside-5'-phosphate esters are shown in Table 13. Produced nucleotide contained only nucleoside-5'-phosphate ester. By-production of nucleoside-2'-phosphate ester and nucleoside-3'-phosphate ester was not observed at all.

TABLE 13

| Nucleoside | Product | Produced amount (g/dl) |
| --- | --- | --- |
| Inosine | 5'-inosinic acid | 7.45 |
| Guanosine | 5'-guanylic acid | 4.77 |
| Uridine | 5'-uridylic acid | 8.93 |
| Cytidine | 5'-cytidylic acid | 6.60 |

EXAMPLE 22
Production of 5'-Inosinic Acid from Various Phosphate Compounds as Phosphate Group Donors by Using The Strains Horboring A Gene Encoding The Acid Phosphatase with Lowered Phosphomonoesterase Activity

*Escherichia coli* JM109/pEPI330 into which the plasmid containing the mutant acid phosphatase gene had been introduced was inoculated to an L medium (50 ml) containing 100 μg/ml of ampicillin and 1 mM of IPTG, and it was cultivated at 37° C. for 16 hours.

Inosine (6 g/dl) and sodium tripolyphosphate, sodium polyphosphate (trade name: Polygon P, produced by Chiyoda Chemical), disodium phenylphosphate, or disodium carbamyl phosphate (12 g/dl) as a phosphate group donor were dissolved in 100 mM sodium acetate buffer (pH 4.0), to which the microbial cells described above were added to give a cell concentration of 200 mg/dl as converted into a dry weight of the cells. The reaction mixture was incubated at 35° C. for 32 hours while maintaining pH at 4.0. The amount of produced 5'-inosinic acid is shown in Table 14. 5'-Inosinic acid was efficiently produced and accumulated by using any of the phosphate group donors. However, the accumulated amount of 5'-inosinic acid was the highest when polyphosphoric acid was used as the phosphate group donor.

TABLE 14

| Phosphate group donor | Produced 5'-inosinic acid (g/dl) |
| --- | --- |
| Sodium tripolyphosphate | 5.96 |
| Sodium polyphosphate | 8.84 |
| Disodium phenylphosphate | 7.60 |
| Disodium carbamyl phosphate | 7.73 |

EXAMPLE 23
Isolation of Acid Phosphatase Gene Derived from Chromosome of *Providencia stuartii* and Determination of Nucleotide Sequence of the Gene Oligonucleotides, PRP1 and PRP2, having nucleotide sequences illustrated in SEQ ID NO: 15 and 16 in Sequence Listing, respectively, were synthesized. These oligonucleotides are designed to amplify a gene coding for acid phosphatase of *Providencia stuartii* on the basis of known nucleotide sequence of the gene coding for acid phosphatase of *Providencia stuartii* (Database of EMBL Accession number X64820).

Chromosomal DNA was extracted from cultivated microbial cells of *Providencia stuartii* ATCC 29851 in accordance with a method of Murray and Thomson (*Nucl. Acid Res.*, 4321, 8 (1980)). The chromosomal DNA (0.1 ng) as a template, oligonucleotides PRP1 and PRP2 (each 2.5 μmol) as primers, and Taq DNA polymerase (2.5 units, produced by Takara Shuzo) were added to 100 mM Tris-HCl buffer (pH 8.3, 100 μl) containing dATP, dCTP, dGTP, dTTP (each 200 μM), potassium chloride (50 mM), and magnesium chloride (1.5 mM) to perform a PCR reaction in which a cycle comprising periods of 30 seconds at 94° C., 2 minutes at 55° C., and 3 minutes at 72° C. was repeated 30 times. The reaction solution was subjected to agarose gel electrophoresis, followed by recovering the amplified DNA fragment of about 1 kbp by means of glass powders (made by Takara Shuzo). The gene fragment was digested with BamHI, which was ligated with pUC118 degiested with BamHI. The plasmid obtained as described above was designated as pPRP100.

Phosphomonoesterase activity and transphosphorylation activity of *Escherichia coli* JM109/pPRP100, a transformant to which pPRP100 was introduced, were mesured. As a result, the strain showed an activity to transphosphorylate to nucleoside as well as phosphomonoesterase activity.

The plasmid was extracted in accordance with the alkaline lysis method from the transformant of *Escherichia coli* JM109/pPRP100 to determine the nucleotide sequence. A nucleotide sequence of a determined open reading frame and an amino acid sequence of the protein deduced from the nucleotide sequence are shown in SEQ ID NO: 17 and 18 in Sequence Listing. The nucleotide sequence of the open reading frame is completely coincident with the nucleotide sequence of the known acid phosphatase gene of *Providencia stuartii*.

EXAMPLE 24
Isolation of Acid Phosphatase Genes Derived from Chromosomes of *Enterobacter aerogenes*, *Klebsiella planticola* and *Serratia ficaria* and Determination of Nucleotide Sequences of the Genes Chromosomal DNA was extracted from cultivated microbial cells of *Enterobacter aerogenes* IFO 12010, *Klebsiella planticola* IFO 14939 and *Serratia ficaria* IAM 13540 in accordance with a method of Murray and Thomson (*Nucl. Acid Res.*, 4321, 8 (1980)). Then, in accordance with the method described in Example 7, a chromosomal gene expression library comprising about 20,000 transformants of Escherichia coli JM109 was constructed and screened to obtain transformants which showed transphosphorylation activity. It was considered that each of these transformants harbours the acid phosphatase gene derived from each of the original strains.

Plasmid DNA was extracted from one of the transformants of Escherichia coli which was considered to have the acid phosphatase gene derived from Enterobacter aerogenes IFO 12010 in accordance with an alkaline lysis method and the inserted DNA of the plasmid was analyzed. The above plasmid was designated as pENP100. A restriction enzyme map of the inserted DNA derived from Enterobacter aerogenes IFO 12010 is shown in FIG. 9.

As a result of specifying the region of acid phosphatase gene by subcloning, it was suggested that the acid phosphatase gene is contained in the 1.6 kbp fragment excised by restriction enzymes SalI and KpnI. Then, the SalI- KpnI fragment was ligated with pUC118 which was digested with SalI and KpnI to construct a plasmid. The resulting plasmid was designated as pENP110.

Figure 10:
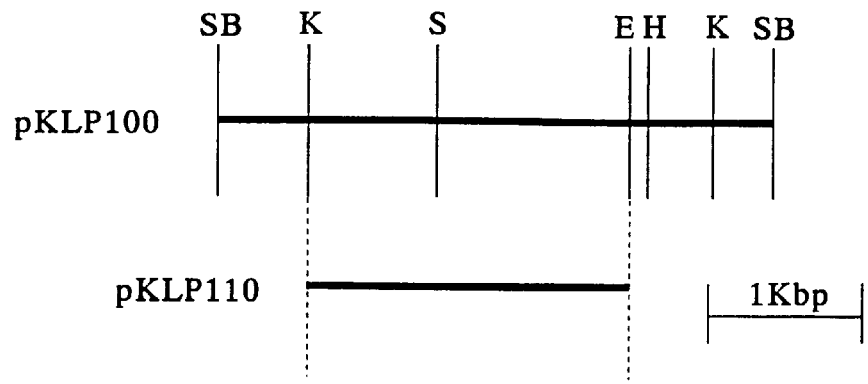
FIG. 10 illustrates a restriction enzyme map of a chromosomal DNA fragment derived from *Klebsiella planticola* which contains the gene coding for acid phosphatase.

According to the procedure as described above, plasmid DNA was extracted from one of the transformants of Escherichia coli which was considered to have the acid phosphatase gene derived from Klebsiella planticola IFO 14939 in accordance with an alkaline lysis method and the insert DNA of the plasmid was analyzed. The above plasmid was designated as pKLP100. A restriction enzyme map of the inserted DNA derived from Klebsiella planticola IFO 14939 is shown in FIG. 10.

As a result of specifying the region of acid phosphatase gene by subcloning, it was suggested that the acid phosphatase gene is contained in the 2.2 kbp fragment excised by restriction enzymes KpnI andEcoRI. Then, the KpnI- EcoRI fragment was ligated with pUC118 which was digested with KpnI and EcoRI to construct a plasmid. The resulting plasmid was designated as pKLP110.

Figure 11:
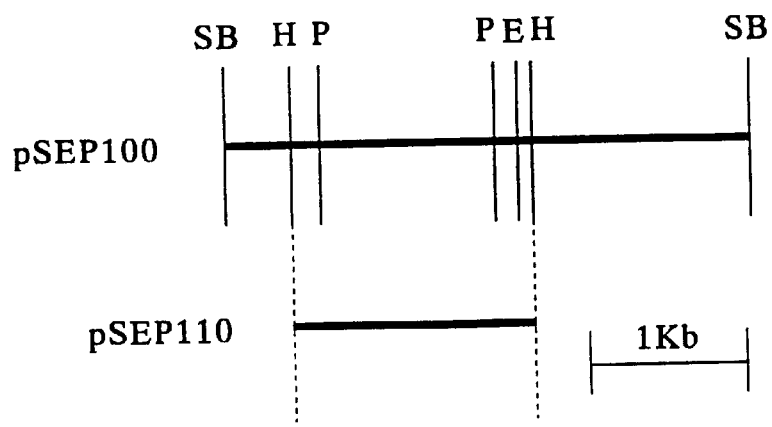
FIG. 11 illustrates a restriction enzyme map of a chromosomal DNA fragment derived from *Serratia ficaria* which contains the gene coding for acid phosphatase.

Similarly, plasmid DNA was extracted from one of the transformants of Escherichia coli which was considered to have the acid phosphatase gene derived from Serratia ficaria IAM 13540 in accordance with an alkaline lysis method and the inserted DNA of the plasmid was analyzed. The above plasmid was designated as pSEP100. A restriction enzyme map of the inserted DNA derived from Serratia ficaria IAM 13540 is shown in FIG. 11.

As a result of specifying the region of acid phosphatase gene by subcloning, it was suggested that the acid phosphatase gene is contained in the 1.4 kbp fragment excised by restriction enzymes HindIII. Then, the HindIII fragment was ligated with pUC118 which was digested with HindIII to construct a plasmid. The resulting plasmid was designated as pSEP110.

Then, the plasmid DNAs were extracted from the transformants, Escherichia coli JM109/pENP110, Escherichia coli JM109/pKLP110 and Escherichia coli JM109/pSEP110, to which pENP110 pKLP110 and pSEP110 had been introduced, respectively, in accordance with an alkaline lysis method. The nucleotide sequences of inserts of these plasmids were determined in accordance with the method described in Example 8. The determined nucleotide sequences of open reading frames of the inserts are shown in SEQ ID NO :19 for Enterobacter aerogenes IFO 12010, in SEQ ID NO: 21 for Klebsiella planticola IFO 14939 and in SEQ ID NO: 23 for Serratia ficaria IAM 13540. Additionally, the deduced amino acid sequences are shown in SEQ ID NOs: 20, 22 and 24, respectively. Because of the fact that the transformants harboring the plasmids containing these fragments exhibited the transphosphorylation activity, it was identified that these open reading frames were the objective acid phosphatase genes.

The nucleotide sequences and the deduced amino acid sequences were respectively compared with known sequences for homology. Data bases of EMBL and SWISS-PROT were used. As a result, it has been revealed that the genes illustrated in SEQ ID NO: 19, 21 and 23 in Sequence Listing are novel genes. It is assumed that the protein encoded by the gene derived from Enterobacter aerogenes IFO 12010 comprises 248 amino acid residues, the protein encoded by the gene derived from Klebsiella planticola IFO 14939 comprises 248 amino acid residues and the protein encoded by the gene derived from Serratia ficaria IAM 13540 comprises 244 amino acid residues. There is a possibility that these proteins may be precursor proteins like the acid phosphatases derived from Morganella morganii and Escherichia blattae.

The amino acid sequences deduced from the nucleotide sequences are shown in FIG. 12 in one-letter together with the deduced amino acid sequence of the acid phosphatase derived from Morganella morganii NCIMB 10466 obtained in Example 8, that of Escherichia blattae JCM 1650 obtained in Example 16 and the known amino acid sequence of the acid phosphatase of Providencia stuartii (EMBL Accession number X64820). Common amino acid residues among all of the amino acids sequences are indicated with asterisks under the sequences in FIG. 12.

As shown in FIG. 12, the amino acid sequences of the acid phosphatases derived from six strains are highly homologous each other and 130 amino acid residues are common among all of the amino acid sequences. Thus, it is assumed that these acid phosphatases have similar functions.

EXAMPLE 25

Amplification of Activity by Expressing Gene of Acid Phosphatase Derived from Enterobacter aerogenes, Klebsiella planticola and Serratia ficaria Escherichia coli JM109/pPRP100 constructed in Example 23, Escherichia coli JM109/pENP110, Escherichia coli JM109/pKLP110 and Escherichia coli JM109/pSEP110 constructed in Example 24 were inoculated to an L-medium (50 ml) containing 100 $\mu$g/ml of ampicillin and 1 mM of IPTG, and were cultivated at 37° C. for 16 hours. Microbial cells were harvested from these cultures by centrifugation, and they were washed once with physiological saline. The microbial cells were suspended in 100 mM potassium phosphate buffer (5 ml, pH 7.0), and they were disrupted by means of a ultrasonic treatment performed at 4° C. for 20 minutes. The treated solutions were centrifuged to remove an insoluble fraction, and thus cell-free extracts were prepared.

The transphosphorylation activities of the obtained cell-free extracts were measured while using controls of cell-free extracts prepared from Providencia stuartii ATCC 29851, Enterobacter aerogenes IFO 12010, Klebsiella planticola IFO 14939, Serratia ficaria IAM 13450, and Escherichia coli JM109 transformed with the plasmid pUC118 in the same manner as described above. Results are shown in Table 15. The transphosphorylation activities were low in all of the wild type strains. The transphosphorylation activity was not detected in Escherichia coli JM109/pUC118. On the other hand, the transformants of Escherichia coli JM109 to which the acid phosphatase genes were introduced exhibited high transphosphorylation activities in comparison with wild type strains. According to the result, it has been demonstrated that each of the introduced DNA fragment allow Escherichia coli to express the acid phosphatase at a high level.

TABLE 15

| Microbial strain | Transphosphrylation Activity (units/mg) |
| --- | --- |
| *Providencia stuartii* ATCC 29851 | 0.005 |
| *Enterobacter aerogenes* IFO 12010 | 0.002 |
| *Klebsiella planticola* IFO 14939 | 0.002 |
| *Serratia ficaria* IAM 13450 | 0.001 |
| *Escherichia coli* JM109/pUC118 | not detected |
| *Escherichia coli* JM109/pPRP100 | 0.833 |
| *Escherichia coli* JM109/pENP110 | 0.301 |
| *Escherichia coli* JM109/pKLP110 | 0.253 |
| *Escherichia coli* JM109/pSEP110 | 0.123 |

Industrial Applicability

According to the present invention, nucleoside-5'-phosphate ester can be produced inexpensively and efficiently by allowing the acid phosphatase to act under the condition of pH 3.0 to 5.5 on a nucleoside and a phosphate group donor selected from the group consisting of polyphosphoric acid or a salt thereof, phenylphosphoric acid or a salt thereof, and carbamyl phosphate or a salt thereof. Especially, nucleoside-5'-phosphate ester can be produced more efficiently by using the acid phosphatase provided by the present invention, the acid phosphatase having the mutation to lower the phosphomonoesterase activity.

What is claimed is:

1. A method for producing nucleoside-5'-phosphate ester comprising the steps of:
reacting a nucleoside and a phosphate group donor selected from the group consisting of polyphosphoric acid or a salt thereof, phenylphosphoric acid or a salt thereof, and carbamyl phosphate or salt thereof in the presence of an acid phosphatase in a solution having a pH of 3.0 to 5.5 to produce nucleoside-5'-phosphate ester, and recovering the nucleoside-5'-phosphate ester from the solution.

2. The method for producing nucleoside-5'-phosphate ester according to claim 1, wherein the acid phosphatase has mutation to lower its phosphomonoesterase activity.

3. The method for producing nucleoside-5'-phosphate ester according to claim 1, wherein the acid phosphatase comprises an amino acid sequence which is selected from the group consisting of sequences illustrated in SEQ ID NOs: 4, 11, 18, 20, 22 and 24 in Sequence Listing, or which is substantially identical with an amino acid sequence selected from said sequences in Sequence Listing.

4. The method for producing nucleoside-5'-phosphate ester according to claim 2, wherein said acid phosphatase comprises an amino acid sequence which is substantially identical with an amino acid sequence selected from the group consisting of sequences illustrated in SEQ ID NOs: 4, 11, 18, 20, 22 and 24 in Sequence Listing, and said acid phosphatase has mutation which lowers phosphomonoesterase activity of an acid phosphatase which comprises an amino acid sequence selected from said sequences in Sequence Listing.

5. The method for producing nucleoside-5'-phosphate ester according to claim 4, wherein said mutation is selected from the group consisting of substitutions of amino acid residue corresponding to substitution(s) of the 72th glycine residue and/or the 151th isoleucine residue with another amino acid in SEQ ID NO: 4 in Sequence Listing.

6. The method for producing nucleoside-5'-phosphate ester according to claim 5, wherein said mutation is selected from the group consisting of substitution(s) of the 72th glycine residue and/or the 151th isoleucine residue with another amino acid in SEQ ID NO: 4 in Sequence Listing, substitution(s) of the 74th glycine residue and/or the 153th isoleucine residue with another amino acid in SEQ ID NO: 11 in Sequence Listing, substitution(s) of the 92th glycine residue and/or the 171th isoleucine residue with another amino acid in SEQ ID NO: 18, 20 or 22 in Sequence Listing, and substitution(s) of the 88th glycine residue and/or the 167th isoleucine residue with another amino acid in SEQ ID NO: 24 in Sequence Listing.

7. A mutant acid phosphatase comprising the amino acid sequence of SEQ ID NO: 4, in which the glycine residue at position 72 is substituted with an amino acid other than glycine and/or the isoleucine residue at position 151 is substituted with an amino acid other than isoleucine, and the mutant acid phosphatase has a lower phosphomonoesterase activity than SEQ ID NO: 4.

8. A mutant acid phosphatase comprising the amino acid sequence of SEQ ID NO: 11, in which the glycine residue at position 74 is substituted with an amino acid other than glycine and/or the isoleucine residue at position 153 is substituted with an amino acid other than isoleucine, and the mutant acid phosphatase has a lower phosphomonoesterase activity than SEQ ID NO: 11.

9. A mutant acid phosphatase comprising an amino acid sequence selected from the group consisting of SEQ ID NO: 18, SEQ ID NO: 20 and SEQ ID NO: 22, in which the glycine residue at position 92 is substituted with an amino acid other than glycine and/or the isoleucine residue at position 171 is substituted with an amino acid other than isoleucine, and the mutant acid phosphatase has a lower phosphomonoesterase activity than said amino acid sequence selected from the group consisting of SEQ ID NO: 18, SEQ ID NO: 20 and SEQ ID NO: 22.

10. A mutant acid phosphatase comprising the amino acid sequence of SEQ ID NO: 24, in which the glycine residue at position 88 is substituted with an amino acid other than glycine and/or the isoleucine residue at position 167 is substituted with an amino acid other than isoleucine, and the mutant acid phosphatase has a lower phosphomonoesterase activity than SEQ ID NO: 24.

11. An acid phosphatase comprising an amino acid sequence selected from the group consisting of SEQ ID NO: 11, SEQ ID NO: 20, SEQ ID NO: 22, and SEQ ID NO: 24.

12. A gene coding for the acid phosphatase as defined in claim 7.

13. A gene coding for the acid phosphatase as defined in claim 8.

14. A gene coding for the acid phosphatase as defined in claim 9.

15. A gene coding for the acid phosphatase as defined in claim 10.

16. A gene coding for the acid phosphatase as defined in claim 11.

17. A recombinant DNA comprising the gene as defined in claim 12.

18. A recombinant DNA comprising the gene as defined in claim 13.

19. A recombinant DNA comprising the gene as defined in claim 14.

20. A recombinant DNA comprising the gene as defined in claim 15.

21. A recombinant DNA comprising the gene as defined in claim 16.

22. A microorganism harboring the recombinant DNA as defined in claim 17.

23. A microorganism harboring the recombinant DNA as defined in claim 18.

24. A microorganism harboring the recombinant DNA as defined in claim 19.

25. A microorganism harboring the recombinant DNA as defined in claim 20.

26. A microorganism harboring the recombinant DNA as defined in claim 21.

27. A method of producing an acid phosphatase, comprising:

culturing the microorganism of claim 22 in a culture medium, and isolating the acid phosphatase.

28. A method of producing an acid phosphatase, comprising:

culturing the microorganism of claim 23 in a culture medium, and isolating the acid phosphatase.

29. A method of producing an acid phosphatase, comprising:

culturing the microorganism of claim 24 in a culture medium, and isolating the acid phosphatase.

30. A method of producing an acid phosphatase, comprising:

culturing the microorganism of claim 25 in a culture medium, and isolating the acid phosphatase.

31. A method of producing an acid phosphatase, comprising:

culturing the microorganism of claim 26 in a culture medium, and isolating the acid phosphatase.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 20 amino acids
      (B) TYPE: amino acid
      (D) TOPOLOGY: linear (ii) MOLECULE TYPE: peptide (v) FRAGMENT TYPE: N-terminal (vi) ORIGINAL SOURCE:
      (A) ORGANISM: Morganella morganii
      (B) STRAIN: NCIMB 10466

(xi) SEQUENCE DESCRIPTION: SEQ ID NO:1:

```
Ala Ile Pro Ala Gly Asn Asp Ala Thr Thr Lys Pro Asp Leu Tyr Tyr
 1               5                  10                  15

Leu Lys Asn Glu
            20
```

(2) INFORMATION FOR SEQ ID NO:2:

(i) SEQUENCE CHARACTERISTICS:
      (A) LENGTH:  750 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Morganella morganii
      (B) STRAIN: NCIMB 10466

(ix) FEATURE:
      (A) NAME/KEY: CDS
      (B) LOCATION: 1..747

(ix) FEATURE:
    (A) NAME/KEY: sig_peptide
    (B) LOCATION: 1..60

(ix) FEATURE:
    (A) NAME/KEY:mat_peptide
    (B) LOCATION:61..747

(xi) SEQUENCE DESCRIPTION: SEQ ID NO:2:

```
ATG AAG AAG AAT ATT ATC GCC GGT TGT CTG TTC TCA CTG TTT TCC CTT       48
Met Lys Lys Asn Ile Ile Ala Gly Cys Leu Phe Ser Leu Phe Ser Leu
-20             -15                 -10                 -5

TCC GCG CTG GCC GCG ATC CCG GCG GGC AAC GAT GCC ACC ACC AAG CCG       96
Ser Ala Leu Ala Ala Ile Pro Ala Gly Asn Asp Ala Thr Thr Lys Pro
                 1                 5                  10

GAT TTA TAT TAT CTG AAA AAT GAA CAG GCT ATC GAC AGC CTG AAA CTG      144
Asp Leu Tyr Tyr Leu Lys Asn Glu Gln Ala Ile Asp Ser Leu Lys Leu
         15                  20                  25

TTA CCG CCA CCG CCG GAA GTC GGC AGT ATT CAG TTT TTA AAT GAT CAG      192
Leu Pro Pro Pro Pro Glu Val Gly Ser Ile Gln Phe Leu Asn Asp Gln
    30                  35                  40

GCA ATG TAT GAG AAA GGC CGT ATG CTG CGC AAT ACC GAG CGC GGA AAA      240
Ala Met Tyr Glu Lys Gly Arg Met Leu Arg Asn Thr Glu Arg Gly Lys
45                  50                  55                  60

CAG GCA CAG GCA GAT GCT GAC CTG GCC GCA GGG GGT GTG GCA ACC GCA      288
Gln Ala Gln Ala Asp Ala Asp Leu Ala Ala Gly Gly Val Ala Thr Ala
                    65                  70                  75

TTT TCA GGG GCA TTC GGC TAT CCG ATA ACC GAA AAA GAC TCT CCG GAG      336
Phe Ser Gly Ala Phe Gly Tyr Pro Ile Thr Glu Lys Asp Ser Pro Glu
            80                  85                  90

CTG TAT AAA CTG CTG ACC AAT ATG ATT GAG GAT GCC GGT GAT CTT GCC      384
Leu Tyr Lys Leu Leu Thr Asn Met Ile Glu Asp Ala Gly Asp Leu Ala
        95                  100                 105

ACC CGC TCC GCC AAA GAA CAT TAC ATG CGC ATC CGG CCG TTT GCG TTT      432
Thr Arg Ser Ala Lys Glu His Tyr Met Arg Ile Arg Pro Phe Ala Phe
    110                 115                 120

TAC GGC ACA GAA ACC TGT AAT ACC AAA GAT CAG AAA AAA CTC TCC ACC      480
Tyr Gly Thr Glu Thr Cys Asn Thr Lys Asp Gln Lys Lys Leu Ser Thr
125                 130                 135                 140

AAC GGA TCT TAC CCG TCA GGT CAT ACG TCT ATC GGC TGG GCA ACC GCA      528
Asn Gly Ser Tyr Pro Ser Gly His Thr Ser Ile Gly Trp Ala Thr Ala
                    145                 150                 155

CTG GTG CTG GCG GAA GTG AAC CCG GCA AAT CAG GAT GCG ATT CTG GAA      576
Leu Val Leu Ala Glu Val Asn Pro Ala Asn Gln Asp Ala Ile Leu Glu
            160                 165                 170

CGG GGT TAT CAG CTC GGA CAG AGC CGG GTG ATT TGC GGC TAT CAC TGG      624
Arg Gly Tyr Gln Leu Gly Gln Ser Arg Val Ile Cys Gly Tyr His Trp
        175                 180                 185

CAG AGT GAT GTG GAT GCC GCG CGG ATT GTC GGT TCA GCC GCT GTC GCG      672
Gln Ser Asp Val Asp Ala Ala Arg Ile Val Gly Ser Ala Ala Val Ala
    190                 195                 200

ACA TTA CAT TCC GAT CCG GCA TTT CAG GCG CAG TTA GCG AAA GCC AAA      720
Thr Leu His Ser Asp Pro Ala Phe Gln Ala Gln Leu Ala Lys Ala Lys
205                 210                 215                 220

CAG GAA TTT GCA CAA AAA TCA CAG AAA TAA                              750
Gln Glu Phe Ala Gln Lys Ser Gln Lys
                225                 229
```

(2) INFORMATION FOR SEQ ID NO:3:

(i) SEQUENCE CHARACTERISTICS:
        (A) LENGTH: 249 amino acids
        (B) TYPE: amino acid (D) TOPOLOGY: linear (ii) MOLECULE TYPE: protein (vi) ORIGINAL SOURCE:
    (A) ORGANISM: Morganella morganii
    (B) STRAIN: NCIMB 10466

(xi) SEQUENCE DESCRIPTION: SEQ ID NO:3:

```
Met Lys Lys Asn Ile Ile Ala Gly Cys Leu Phe Ser Leu Phe Ser Leu
-20             -15                 -10                 -5

Ser Ala Leu Ala Ala Ile Pro Ala Gly Asn Asp Ala Thr Thr Lys Pro
                 1               5                  10

Asp Leu Tyr Tyr Leu Lys Asn Glu Gln Ala Ile Asp Ser Leu Lys Leu
             15                  20                  25

Leu Pro Pro Pro Glu Val Gly Ser Ile Gln Phe Leu Asn Asp Gln
     30              35                  40

Ala Met Tyr Glu Lys Gly Arg Met Leu Arg Asn Thr Glu Arg Gly Lys
 45              50                  55                  60

Gln Ala Gln Ala Asp Ala Asp Leu Ala Ala Gly Gly Val Ala Thr Ala
                 65                  70                  75

Phe Ser Gly Ala Phe Gly Tyr Pro Ile Thr Glu Lys Asp Ser Pro Glu
             80                  85                  90

Leu Tyr Lys Leu Leu Thr Asn Met Ile Glu Asp Ala Gly Asp Leu Ala
             95                  100                 105

Thr Arg Ser Ala Lys Glu His Tyr Met Arg Ile Arg Pro Phe Ala Phe
110                 115                 120

Tyr Gly Thr Glu Thr Cys Asn Thr Lys Asp Gln Lys Lys Leu Ser Thr
125                 130                 135                 140

Asn Gly Ser Tyr Pro Ser Gly His Thr Ser Ile Gly Trp Ala Thr Ala
                145                 150                 155

Leu Val Leu Ala Glu Val Asn Pro Ala Asn Gln Asp Ala Ile Leu Glu
                160                 165                 170

Arg Gly Tyr Gln Leu Gly Gln Ser Arg Val Ile Cys Gly Tyr His Trp
                175                 180                 185

Gln Ser Asp Val Asp Ala Ala Arg Ile Val Gly Ser Ala Ala Val Ala
190                 195                 200

Thr Leu His Ser Asp Pro Ala Phe Gln Ala Gln Leu Ala Lys Ala Lys
205                 210                 215                 220

Gln Glu Phe Ala Gln Lys Ser Gln Lys
                225                 229
```

(2) INFORMATION FOR SEQ ID NO:4:

(i) SEQUENCE CHARACTERISTICS:
        (A) LENGTH: 229 amino acids
        (B) TYPE: amino acid
        (D) TOPOLOGY: linear (ii) MOLECULE TYPE: protein (vi) ORIGINAL SOURCE:
        (A) ORGANISM: Morganella morganii
        (B) STRAIN: NCIMB 10466

(xi) SEQUENCE DESCRIPTION: SEQ ID NO:4:

```
Ala Ile Pro Ala Gly Asn Asp Ala Thr Thr Lys Pro Asp Leu Tyr Tyr
 1               5                  10                  15

Leu Lys Asn Glu Gln Ala Ile Asp Ser Leu Lys Leu Leu Pro Pro Pro
             20                  25                  30
```

```
Pro Glu Val Gly Ser Ile Gln Phe Leu Asn Asp Gln Ala Met Tyr Glu
             35                  40                  45
Lys Gly Arg Met Leu Arg Asn Thr Glu Arg Gly Lys Gln Ala Gln Ala
 50                  55                  60
Asp Ala Asp Leu Ala Ala Gly Gly Val Ala Thr Ala Phe Ser Gly Ala
 65                  70                  75                  80
Phe Gly Tyr Pro Ile Thr Glu Lys Asp Ser Pro Glu Leu Tyr Lys Leu
                 85                  90                  95
Leu Thr Asn Met Ile Glu Asp Ala Gly Asp Leu Ala Thr Arg Ser Ala
                100                 105                 110
Lys Glu His Tyr Met Arg Ile Arg Pro Phe Ala Phe Tyr Gly Thr Glu
                115                 120                 125
Thr Cys Asn Thr Lys Asp Gln Lys Lys Leu Ser Thr Asn Gly Ser Tyr
            130                 135                 140
Pro Ser Gly His Thr Ser Ile Gly Trp Ala Thr Ala Leu Val Leu Ala
145                 150                 155                 160
Glu Val Asn Pro Ala Asn Gln Asp Ala Ile Leu Glu Arg Gly Tyr Gln
                165                 170                 175
Leu Gly Gln Ser Arg Val Ile Cys Gly Tyr His Trp Gln Ser Asp Val
                180                 185                 190
Asp Ala Ala Arg Ile Val Gly Ser Ala Ala Val Ala Thr Leu His Ser
            195                 200                 205
Asp Pro Ala Phe Gln Ala Gln Leu Ala Lys Ala Lys Gln Glu Phe Ala
210                 215                 220
Gln Lys Ser Gln Lys
225                 229

(2) INFORMATION FOR SEQ ID NO:5:

(i) SEQUENCE CHARACTERISTICS:
        (A) LENGTH:  20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(iii) HYPOTHETICAL: NO (iv) ANTI-SENSE: NO (xi) SEQUENCE DESCRIPTION: SEQ ID NO:5:

ATTACCATGA TTACGAATTC                                              20

(2) INFORMATION FOR SEQ ID NO:6:

(i) SEQUENCE CHARACTERISTICS:
        (A) LENGTH:  21 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(iii) HYPOTHETICAL: NO (iv) ANTI-SENSE: YES (xi) SEQUENCE DESCRIPTION: SEQ ID NO:6:

GCGGTTGCCA CATCCCCTGC G                                            21
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iii) HYPOTHETICAL: NO (iv) ANTI-SENSE: NO (xi) SEQUENCE DESCRIPTION: SEQ ID NO:7:

```
TTGCCCAGCC GGTAGACGTA T                                           21
```

(2) INFORMATION FOR SEQ ID NO:8:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: N-terminal (vi) ORIGINAL SOURCE:
        (A) ORGANISM: Escherichia blattae
        (B) STRAIN: JCM 1650

(xi) SEQUENCE DESCRIPTION: SEQ ID NO:8:

```
Leu Ala Leu Val Ala Thr Gly Asn Asp Thr Thr Thr Lys Pro Asp Leu
 1               5                  10                  15
```

(2) INFORMATION FOR SEQ ID NO:9:

(i) SEQUENCE CHARACTERISTICS:
        (A) LENGTH: 750 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Escherichia blattae
        (B) STRAIN: JCM 1650

(ix) FEATURE:
        (A) NAME/KEY: CDS
        (B) LOCATION: 1..747

(ix) FEATURE:
        (A) NAME/KEY: sig_peptide
        (B) LOCATION: 1..54

(ix) FEATURE:
        (A) NAME/KEY:mat_peptide
        (B) LOCATION:55..747

(xi) SEQUENCE DESCRIPTION: SEQ ID NO:9:

```
ATG AAA AAA CGT GTT CTG GCA GTT TGT TTT GCC GCA TTG TTC TCT TCT      48
Met Lys Lys Arg Val Leu Ala Val Cys Phe Ala Ala Leu Phe Ser Ser
-18         -15                 -10                 -5

CAG GCC CTG GCG CTG GTC GCT ACC GGC AAC GAC ACT ACC ACG AAA CCG      96
Gln Ala Leu Ala Leu Val Ala Thr Gly Asn Asp Thr Thr Thr Lys Pro
  1               5                  10
```

```
GAT CTC TAC TAC CTC AAG AAC AGT GAA GCC ATT AAC AGC CTG GCG CTG    144
Asp Leu Tyr Tyr Leu Lys Asn Ser Glu Ala Ile Asn Ser Leu Ala Leu
 15              20                  25                  30

TTG CCG CCA CCA CCG GCG GTG GGC TCC ATT GCG TTT CTC AAC GAT CAG    192
Leu Pro Pro Pro Ala Val Gly Ser Ile Ala Phe Leu Asn Asp Gln
             35                  40                  45

GCC ATG TAT GAA CAG GGG CGC CTG CTG CGC AAC ACC GAA CGC GGT AAG    240
Ala Met Tyr Glu Gln Gly Arg Leu Leu Arg Asn Thr Glu Arg Gly Lys
         50                  55                  60

CTG GCG GCG GAA GAT GCA AAC CTG AGC AGT GGC GGG GTG GCG AAT GCT    288
Leu Ala Ala Glu Asp Ala Asn Leu Ser Ser Gly Gly Val Ala Asn Ala
     65                  70                  75

TTC TCC GGC GCG TTT GGT AGC CCG ATC ACC GAA AAA GAC GCC CCG GCG    336
Phe Ser Gly Ala Phe Gly Ser Pro Ile Thr Glu Lys Asp Ala Pro Ala
 80                  85                  90

CTG CAT AAA TTA CTG ACC AAT ATG ATT GAG GAC GCC GGG GAT CTG GCG    384
Leu His Lys Leu Leu Thr Asn Met Ile Glu Asp Ala Gly Asp Leu Ala
 95                 100                 105                 110

ACC CGC AGC GCG AAA GAT CAC TAT ATG CGC ATT CGT CCG TTC GCG TTT    432
Thr Arg Ser Ala Lys Asp His Tyr Met Arg Ile Arg Pro Phe Ala Phe
             115                 120                 125

TAT GGG GTC TCT ACC TGT AAT ACC ACC GAG CAG GAC AAA CTG TCC AAA    480
Tyr Gly Val Ser Thr Cys Asn Thr Thr Glu Gln Asp Lys Leu Ser Lys
         130                 135                 140

AAT GGC TCT TAT CCG TCC GGG CAT ACC TCT ATC GGC TGG GCT ACT GCG    528
Asn Gly Ser Tyr Pro Ser Gly His Thr Ser Ile Gly Trp Ala Thr Ala
     145                 150                 155

CTG GTG CTG GCA GAG ATC AAC CCT CAG CGC CAG AAC GAG ATC CTG AAA    576
Leu Val Leu Ala Glu Ile Asn Pro Gln Arg Gln Asn Glu Ile Leu Lys
 160                 165                 170

CGC GGT TAT GAG CTG GGC CAG AGC CGG GTG ATT TGC GGC TAC CAC TGG    624
Arg Gly Tyr Glu Leu Gly Gln Ser Arg Val Ile Cys Gly Tyr His Trp
175                 180                 185                 190

CAG AGT GAT GTG GAT GCC GCG CGG GTA GTG GGA TCT GCC GTT GTG GCG    672
Gln Ser Asp Val Asp Ala Ala Arg Val Val Gly Ser Ala Val Val Ala
             195                 200                 205

ACC CTG CAT ACC AAC CCG GCG TTC CAG CAG CAG TTG CAG AAA GCG AAG    720
Thr Leu His Thr Asn Pro Ala Phe Gln Gln Gln Leu Gln Lys Ala Lys
         210                 215                 220

GCC GAA TTC GCC CAG CAT CAG AAG AAA TAA                            750
Ala Glu Phe Ala Gln His Gln Lys Lys
     225                 230

(2) INFORMATION FOR SEQ ID NO:10:

(i) SEQUENCE CHARACTERISTICS:
        (A) LENGTH: 249 amino acids
        (B) TYPE: amino acid
        (D) TOPOLOGY: linear (ii) MOLECULE TYPE: protein (vi) ORIGINAL SOURCE:
         (A) ORGANISM: Escherichia blattae
         (B) STRAIN: JCM 1650

(xi) SEQUENCE DESCRIPTION: SEQ ID NO:10:

Met Lys Lys Arg Val Leu Ala Val Cys Phe Ala Ala Leu Phe Ser Ser
-18             -15                 -10                 -5

Gln Ala Leu Ala Leu Val Ala Thr Gly Asn Asp Thr Thr Thr Lys Pro
         1               5                  10

Asp Leu Tyr Tyr Leu Lys Asn Ser Glu Ala Ile Asn Ser Leu Ala Leu
```

-continued

```
              15                  20                  25                  30
Leu Pro Pro Pro Ala Val Gly Ser Ile Ala Phe Leu Asn Asp Gln
                35                  40                  45
Ala Met Tyr Glu Gln Gly Arg Leu Leu Arg Asn Thr Glu Arg Gly Lys
        50                  55                  60
Leu Ala Ala Glu Asp Ala Asn Leu Ser Ser Gly Gly Val Ala Asn Ala
            65                  70                  75
Phe Ser Gly Ala Phe Gly Ser Pro Ile Thr Glu Lys Asp Ala Pro Ala
            80                  85                  90
Leu His Lys Leu Leu Thr Asn Met Ile Glu Asp Ala Gly Asp Leu Ala
95                  100                 105                 110
Thr Arg Ser Ala Lys Asp His Tyr Met Arg Ile Arg Pro Phe Ala Phe
            115                 120                 125
Tyr Gly Val Ser Thr Cys Asn Thr Thr Glu Gln Asp Lys Leu Ser Lys
            130                 135                 140
Asn Gly Ser Tyr Pro Ser Gly His Thr Ser Ile Gly Trp Ala Thr Ala
            145                 150                 155
Leu Val Leu Ala Glu Ile Asn Pro Gln Arg Gln Asn Glu Ile Leu Lys
    160                 165                 170
Arg Gly Tyr Glu Leu Gly Gln Ser Arg Val Ile Cys Gly Tyr His Trp
175                 180                 185                 190
Gln Ser Asp Val Asp Ala Ala Arg Val Val Gly Ser Ala Val Val Ala
                195                 200                 205
Thr Leu His Thr Asn Pro Ala Phe Gln Gln Leu Gln Lys Ala Lys
                210                 215                 220
Ala Glu Phe Ala Gln His Gln Lys Lys
            225                 230

(2) INFORMATION FOR SEQ ID NO:11:

(i) SEQUENCE CHARACTERISTICS:
        (A) LENGTH: 231 amino acids
        (B) TYPE: amino acid
        (D) TOPOLOGY: linear (ii) MOLECULE TYPE: protein (vi) ORIGINAL SOURCE:
        (A) ORGANISM: Escherichia blattae
        (B) STRAIN: JCM 1650

(xi) SEQUENCE DESCRIPTION: SEQ ID NO:11:

Leu Ala Leu Val Ala Thr Gly Asn Asp Thr Thr Thr Lys Pro Asp Leu
1               5                   10                  15
Tyr Tyr Leu Lys Asn Ser Glu Ala Ile Asn Ser Leu Ala Leu Leu Pro
            20                  25                  30
Pro Pro Pro Ala Val Gly Ser Ile Ala Phe Leu Asn Asp Gln Ala Met
        35                  40                  45
Tyr Glu Gln Gly Arg Leu Leu Arg Asn Thr Glu Arg Gly Lys Leu Ala
    50                  55                  60
Ala Glu Asp Ala Asn Leu Ser Ser Gly Gly Val Ala Asn Ala Phe Ser
65              70                  75                  80
Gly Ala Phe Gly Ser Pro Ile Thr Glu Lys Asp Ala Pro Ala Leu His
            85                  90                  95
Lys Leu Leu Thr Asn Met Ile Glu Asp Ala Gly Asp Leu Ala Thr Arg
        100                 105                 110
Ser Ala Lys Asp His Tyr Met Arg Ile Arg Pro Phe Ala Phe Tyr Gly
    115                 120                 125
```

```
Val Ser Thr Cys Asn Thr Thr Glu Gln Asp Lys Leu Ser Lys Asn Gly
        130                 135                 140

Ser Tyr Pro Ser Gly His Thr Ser Ile Gly Trp Ala Thr Ala Leu Val
145                 150                 155                 160

Leu Ala Glu Ile Asn Pro Gln Arg Gln Asn Glu Ile Leu Lys Arg Gly
                165                 170                 175

Tyr Glu Leu Gly Gln Ser Arg Val Ile Cys Gly Tyr His Trp Gln Ser
                180                 185                 190

Asp Val Asp Ala Ala Arg Val Val Gly Ser Ala Val Val Ala Thr Leu
                195                 200                 205

His Thr Asn Pro Ala Phe Gln Gln Leu Gln Lys Ala Lys Ala Glu
        210                 215                 220

Phe Ala Gln His Gln Lys Lys
225                 230
```

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iii) HYPOTHETICAL: NO (iv) ANTI-SENSE: NO (xi) SEQUENCE DESCRIPTION: SEQ ID NO:12:

CCTCGAGGTC GACGGTATCG                                      20

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iii) HYPOTHETICAL: NO (iv) ANTI-SENSE: YES (xi) SEQUENCE DESCRIPTION: SEQ ID NO:13:

ATTCGCCACA TCGCCACTGC T                                    21

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iii) HYPOTHETICAL: NO (iv) ANTI-SENSE: NO (xi) SEQUENCE DESCRIPTION: SEQ ID NO:14:

```
                                      -continued

TAGCCCAGCC GGTAGAGGTA TG                                              22

(2) INFORMATION FOR SEQ ID NO:15:

(i) SEQUENCE CHARACTERISTICS:
         (A) LENGTH:  25 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(iii) HYPOTHETICAL: NO (iv) ANTI-SENSE: YES (xi) SEQUENCE DESCRIPTION: SEQ ID NO:15:

CTGGATCCTG TGGCTATCAT CACCT                                           25

(2) INFORMATION FOR SEQ ID NO:16:

(i) SEQUENCE CHARACTERISTICS:
         (A) LENGTH:  25 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(iii) HYPOTHETICAL: NO (iv) ANTI-SENSE: NO (xi) SEQUENCE DESCRIPTION: SEQ ID NO:16:

CTGGATCCGA CGCGATTTTA CCATA                                           25

(2) INFORMATION FOR SEQ ID NO:17:

(i) SEQUENCE CHARACTERISTICS:
         (A) LENGTH: 747 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Providencia stuartii
         (B) STRAIN: ATCC 29851

(ix) FEATURE:
         (A) NAME/KEY: CDS
         (B) LOCATION: 1..744

(xi) SEQUENCE DESCRIPTION: SEQ ID NO:17:

ATG AAA AAA CTA TTA GCA GTA TTC TGC GCA GGG GCT TTT GTT TCA ACC       48
Met Lys Lys Leu Leu Ala Val Phe Cys Ala Gly Ala Phe Val Ser Thr
 1               5                  10                  15

AGT GTA TTT GCG GCG ATC CCT CCC GGC AAT GAT GTG ACA ACT AAA CCC       96
Ser Val Phe Ala Ala Ile Pro Pro Gly Asn Asp Val Thr Thr Lys Pro
                20                  25                  30

GAT CTT TAT TAT TTA AAA AAC TCA CAG GCT ATT GAT AGT TTA GCG TTA      144
Asp Leu Tyr Tyr Leu Lys Asn Ser Gln Ala Ile Asp Ser Leu Ala Leu
            35                  40                  45

TTG CCG CCA CCA CCT GAA GTG GGC AGT ATC TTA TTT TTA AAC GAC CAA      192
```

```
       Leu Pro Pro Pro Glu Val Gly Ser Ile Leu Phe Leu Asn Asp Gln
            50                  55                  60

GCG ATG TAT GAA AAA GGC CGT TTA TTG CGA AAT ACT GAG CGT GGA GAA       240
       Ala Met Tyr Glu Lys Gly Arg Leu Leu Arg Asn Thr Glu Arg Gly Glu
        65                  70                  75                  80

CAA GCC GCT AAG GAT GCT GAT CTG GCT GCG GGC GGT GTT GCG AAC GCA       288
       Gln Ala Ala Lys Asp Ala Asp Leu Ala Ala Gly Gly Val Ala Asn Ala
                        85                  90                  95

TTT TCT GAA GCT TTT GGT TAT CCC ATT ACC GAA AAG GAT GCG CCT GAA       336
       Phe Ser Glu Ala Phe Gly Tyr Pro Ile Thr Glu Lys Asp Ala Pro Glu
                    100                 105                 110

ATT CAT AAA TTG CTG ACG AAT ATG ATT GAA GAT GCG GGG GAT TTA GCA       384
       Ile His Lys Leu Leu Thr Asn Met Ile Glu Asp Ala Gly Asp Leu Ala
                115                 120                 125

ACT CGC TCA GCC AAA GAG AAA TAC ATG CGC ATT CGT CCA TTT GCG TTC       432
       Thr Arg Ser Ala Lys Glu Lys Tyr Met Arg Ile Arg Pro Phe Ala Phe
       130                 135                 140

TAC GGT GTT GCT ACC TGT AAC ACG AAA GAT CAG GAC AAA TTA TCT AAG       480
       Tyr Gly Val Ala Thr Cys Asn Thr Lys Asp Gln Asp Lys Leu Ser Lys
       145                 150                 155                 160

AAT GGC TCT TAT CCT TCT GGA CAC ACC GCA ATT GGC TGG GCA TCT GCA       528
       Asn Gly Ser Tyr Pro Ser Gly His Thr Ala Ile Gly Trp Ala Ser Ala
                        165                 170                 175

CTC GTA TTG TCA GAA ATT AAC CCA GAA AAC CAA GAT AAA ATT TTA AAA       576
       Leu Val Leu Ser Glu Ile Asn Pro Glu Asn Gln Asp Lys Ile Leu Lys
                    180                 185                 190

CGT GGT TAT GAA CTT GGC CAA AGC CGA GTC ATC TGT GGT TAC CAT TGG       624
       Arg Gly Tyr Glu Leu Gly Gln Ser Arg Val Ile Cys Gly Tyr His Trp
                195                 200                 205

CAA AGT GAT GTT GAT GCA GCT CGT ATC GTT GCA TCG GGT GCG GTA GCA       672
       Gln Ser Asp Val Asp Ala Ala Arg Ile Val Ala Ser Gly Ala Val Ala
       210                 215                 220

ACT TTA CAC TCC AAC CCT GAA TTC CAA AAA CAG TTA CAA AAA GCC AAA       720
       Thr Leu His Ser Asn Pro Glu Phe Gln Lys Gln Leu Gln Lys Ala Lys
       225                 230                 235                 240

GAC GAA TTT GCT AAA CTG AAA AAA TAG                                   747
       Asp Glu Phe Ala Lys Leu Lys Lys
                        245

(2) INFORMATION FOR SEQ ID NO:18:

(i) SEQUENCE CHARACTERISTICS:
            (A) LENGTH: 248 amino acids
            (B) TYPE: amino acid
            (D) TOPOLOGY: linear (ii) MOLECULE TYPE: protein (vi) ORIGINAL SOURCE:
            (A) ORGANISM: Providencia stuartii
            (B) STRAIN: ATCC 29851

(xi) SEQUENCE DESCRIPTION: SEQ ID NO:18:

Met Lys Lys Leu Leu Ala Val Phe Cys Ala Gly Ala Phe Val Ser Thr
    1               5                  10                  15

Ser Val Phe Ala Ala Ile Pro Pro Gly Asn Asp Val Thr Thr Lys Pro
                    20                  25                  30

Asp Leu Tyr Tyr Leu Lys Asn Ser Gln Ala Ile Asp Ser Leu Ala Leu
                35                  40                  45

Leu Pro Pro Pro Glu Val Gly Ser Ile Leu Phe Leu Asn Asp Gln
        50                  55                  60

Ala Met Tyr Glu Lys Gly Arg Leu Leu Arg Asn Thr Glu Arg Gly Glu
```

```
                    65                  70                  75                  80
        Gln Ala Ala Lys Asp Ala Asp Leu Ala Ala Gly Gly Val Ala Asn Ala
                            85                  90                  95

Phe Ser Glu Ala Phe Gly Tyr Pro Ile Thr Glu Lys Asp Ala Pro Glu
                            100                 105                 110

Ile His Lys Leu Leu Thr Asn Met Ile Glu Asp Ala Gly Asp Leu Ala
                            115                 120                 125

Thr Arg Ser Ala Lys Glu Lys Tyr Met Arg Ile Arg Pro Phe Ala Phe
                130                 135                 140

Tyr Gly Val Ala Thr Cys Asn Thr Lys Asp Gln Asp Lys Leu Ser Lys
        145                 150                 155                 160

Asn Gly Ser Tyr Pro Ser Gly His Thr Ala Ile Gly Trp Ala Ser Ala
                            165                 170                 175

Leu Val Leu Ser Glu Ile Asn Pro Glu Asn Gln Asp Lys Ile Leu Lys
                            180                 185                 190

Arg Gly Tyr Glu Leu Gly Gln Ser Arg Val Ile Cys Gly Tyr His Trp
                            195                 200                 205

Gln Ser Asp Val Asp Ala Ala Arg Ile Val Ala Ser Gly Ala Val Ala
                            210                 215                 220

Thr Leu His Ser Asn Pro Glu Phe Gln Lys Gln Leu Gln Lys Ala Lys
        225                 230                 235                 240

Asp Glu Phe Ala Lys Leu Lys Lys
                            245

(2) INFORMATION FOR SEQ ID NO:19:

(i) SEQUENCE CHARACTERISTICS:
            (A) LENGTH:  747 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Enterobacter aerogenes
            (B) STRAIN: IFO 12010

(ix) FEATURE:
            (A) NAME/KEY: CDS
            (B) LOCATION: 1..744

(xi) SEQUENCE DESCRIPTION: SEQ ID NO:19:

ATG AAA AAG CGC GTT CTC GCC CTC TGC CTC GCC AGC CTG TTT TCC GTT        48
Met Lys Lys Arg Val Leu Ala Leu Cys Leu Ala Ser Leu Phe Ser Val
 1               5                  10                  15

AAC GCT TTC GCG CTG GTC CCT GCC GGC AAT GAT GCA ACC ACC AAA CCG        96
Asn Ala Phe Ala Leu Val Pro Ala Gly Asn Asp Ala Thr Thr Lys Pro
            20                  25                  30

GAT CTC TAT TAT CTG AAA AAT GCA CAG GCC ATC GAT AGT CTG GCG CTG       144
Asp Leu Tyr Tyr Leu Lys Asn Ala Gln Ala Ile Asp Ser Leu Ala Leu
        35                  40                  45

TTG CCG CCG CCG CCG GAA GTT GGC AGC ATC GCA TTT TTA AAC GAT CAG       192
Leu Pro Pro Pro Pro Glu Val Gly Ser Ile Ala Phe Leu Asn Asp Gln
 50                  55                  60

GCG ATG TAT GAG AAA GGA CGG CTG TTG CGC AAT ACC GAA CGT GGC AAG       240
Ala Met Tyr Glu Lys Gly Arg Leu Leu Arg Asn Thr Glu Arg Gly Lys
 65                  70                  75                  80
```

-continued

```
CTG GCG GCT GAA GAT GCT AAC CTG AGC GCC GGC GGC GTC GCG AAT GCC       288
Leu Ala Ala Glu Asp Ala Asn Leu Ser Ala Gly Gly Val Ala Asn Ala
                 85                  90                  95

TTC TCC AGC GCT TTT GGT TCG CCC ATC ACC GAA AAA GAC GCG CCG CAG       336
Phe Ser Ser Ala Phe Gly Ser Pro Ile Thr Glu Lys Asp Ala Pro Gln
            100                 105                 110

TTA CAT AAG CTG CTG ACA AAT ATG ATT GAG GAT GCC GGC GAT CTG GCC       384
Leu His Lys Leu Leu Thr Asn Met Ile Glu Asp Ala Gly Asp Leu Ala
            115                 120                 125

ACC CGC AGC GCG AAA GAG AAA TAT ATG CGC ATT CGC CCG TTT GCG TTC       432
Thr Arg Ser Ala Lys Glu Lys Tyr Met Arg Ile Arg Pro Phe Ala Phe
        130                 135                 140

TAC GGC GTT TCA ACC TGT AAC ACT ACC GAG CAG GAC AAG CTG TCG AAA       480
Tyr Gly Val Ser Thr Cys Asn Thr Thr Glu Gln Asp Lys Leu Ser Lys
145                 150                 155                 160

AAC GGA TCT TAC CCT TCC GGC CAT ACC TCT ATC GGT TGG GCA ACC GCG       528
Asn Gly Ser Tyr Pro Ser Gly His Thr Ser Ile Gly Trp Ala Thr Ala
                165                 170                 175

CTG GTA CTG GCG GAG ATC AAT CCG CAG CGG CAA AAC GAA ATT CTC AAA       576
Leu Val Leu Ala Glu Ile Asn Pro Gln Arg Gln Asn Glu Ile Leu Lys
            180                 185                 190

CGC GGC TAT GAA TTG GGC GAA AGC CGG GTT ATC TGC GGC TAT CAT TGG       624
Arg Gly Tyr Glu Leu Gly Glu Ser Arg Val Ile Cys Gly Tyr His Trp
            195                 200                 205

CAG AGC GAT GTC GAT GCG GCG CGG ATA GTC GGC TCG GCG GTG GTG GCG       672
Gln Ser Asp Val Asp Ala Ala Arg Ile Val Gly Ser Ala Val Val Ala
        210                 215                 220

ACC CTG CAT ACC AAC CCG GCC TTC CAA CAG CAG TTG CAG AAA GCA AAG       720
Thr Leu His Thr Asn Pro Ala Phe Gln Gln Gln Leu Gln Lys Ala Lys
225                 230                 235                 240

GAT GAA TTC GCC AAA ACG CAG AAG TAA                                   747
Asp Glu Phe Ala Lys Thr Gln Lys
            245
```

(2) INFORMATION FOR SEQ ID NO:20:

(i) SEQUENCE CHARACTERISTICS:
        (A) LENGTH: 248 amino acids
        (B) TYPE: amino acid
        (D) TOPOLOGY: linear (ii) MOLECULE TYPE: protein (vi) ORIGINAL SOURCE:
        (A) ORGANISM: Enterobacter aerogenes
        (B) STRAIN: IFO 12010

(xi) SEQUENCE DESCRIPTION: SEQ ID NO:20:

```
Met Lys Lys Arg Val Leu Ala Leu Cys Leu Ala Ser Leu Phe Ser Val
  1               5                  10                  15

Asn Ala Phe Ala Leu Val Pro Ala Gly Asn Asp Ala Thr Thr Lys Pro
             20                  25                  30

Asp Leu Tyr Tyr Leu Lys Asn Ala Gln Ala Ile Asp Ser Leu Ala Leu
         35                  40                  45

Leu Pro Pro Pro Glu Val Gly Ser Ile Ala Phe Leu Asn Asp Gln
     50                  55                  60

Ala Met Tyr Glu Lys Gly Arg Leu Leu Arg Asn Thr Glu Arg Gly Lys
 65                  70                  75                  80

Leu Ala Ala Glu Asp Ala Asn Leu Ser Ala Gly Gly Val Ala Asn Ala
                 85                  90                  95

Phe Ser Ser Ala Phe Gly Ser Pro Ile Thr Glu Lys Asp Ala Pro Gln
            100                 105                 110
```

```
Leu His Lys Leu Leu Thr Asn Met Ile Glu Asp Ala Gly Asp Leu Ala
        115                 120                 125

Thr Arg Ser Ala Lys Glu Lys Tyr Met Arg Ile Arg Pro Phe Ala Phe
    130                 135                 140

Tyr Gly Val Ser Thr Cys Asn Thr Thr Glu Gln Asp Lys Leu Ser Lys
145                 150                 155                 160

Asn Gly Ser Tyr Pro Ser Gly His Thr Ser Ile Gly Trp Ala Thr Ala
                165                 170                 175

Leu Val Leu Ala Glu Ile Asn Pro Gln Arg Gln Asn Glu Ile Leu Lys
            180                 185                 190

Arg Gly Tyr Glu Leu Gly Glu Ser Arg Val Ile Cys Gly Tyr His Trp
        195                 200                 205

Gln Ser Asp Val Asp Ala Ala Arg Ile Val Gly Ser Ala Val Val Ala
    210                 215                 220

Thr Leu His Thr Asn Pro Ala Phe Gln Gln Gln Leu Gln Lys Ala Lys
225                 230                 235                 240

Asp Glu Phe Ala Lys Thr Gln Lys
                245
```

(2) INFORMATION FOR SEQ ID NO:21:

(i) SEQUENCE CHARACTERISTICS:
        (A) LENGTH: 747 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Klevsiella planticola
        (B) STRAIN: IFO 14939

(ix) FEATURE:
        (A) NAME/KEY: CDS
        (B) LOCATION: 1..747

(xi) SEQUENCE DESCRIPTION: SEQ ID NO:21:

```
ATG AAA AAG CGT GTA CTC GCC CTT TGC CTT GCC AGC CTC TTT TCA GTT      48
Met Lys Lys Arg Val Leu Ala Leu Cys Leu Ala Ser Leu Phe Ser Val
 1               5                  10                  15

AGC GCC TTT GCG CTG GTT CCC GCC GGC AAT GAT GCC ACC ACC AAG CCC      96
Ser Ala Phe Ala Leu Val Pro Ala Gly Asn Asp Ala Thr Thr Lys Pro
             20                  25                  30

GAT CTC TAC TAT CTG AAA AAT GCC CAG GCC ATT GAC AGC CTG GCG CTG     144
Asp Leu Tyr Tyr Leu Lys Asn Ala Gln Ala Ile Asp Ser Leu Ala Leu
         35                  40                  45

TTG CCA CCG CCG CCG GAA GTG GGC AGC ATT GCG TTT TTA AAC GAT CAG     192
Leu Pro Pro Pro Pro Glu Val Gly Ser Ile Ala Phe Leu Asn Asp Gln
     50                  55                  60

GCG ATG TAT GAG AAA GGC CGT CTG CTG CGC GCC ACC GCC CGC GGC AAG     240
Ala Met Tyr Glu Lys Gly Arg Leu Leu Arg Ala Thr Ala Arg Gly Lys
 65                  70                  75                  80

TTG GCG GCA GAA GAT GCC AAC CTG AGC GCG GGT GGC GTG GCC AAC GCC     288
Leu Ala Ala Glu Asp Ala Asn Leu Ser Ala Gly Gly Val Ala Asn Ala
                 85                  90                  95

TTC TCC GCA GCA TTC GGC TCC CCG ATC AGC GAA AAA GAC GCC CCG GCG     336
Phe Ser Ala Ala Phe Gly Ser Pro Ile Ser Glu Lys Asp Ala Pro Ala
            100                 105                 110
```

```
CTG CAC AAA CTG CTC ACC AAC ATG ATT GAA GAC GCG GGC GAT CTG GCG        384
Leu His Lys Leu Leu Thr Asn Met Ile Glu Asp Ala Gly Asp Leu Ala
        115                 120                 125

ACC CGA GGC GCG AAA GAG AAG TAT ATG CGT ATT CGT CCG TTT GCC TTC        432
Thr Arg Gly Ala Lys Glu Lys Tyr Met Arg Ile Arg Pro Phe Ala Phe
130                 135                 140

TAC GGC GTG TCC ACC TGC AAT ACC ACC GAA CAG GAT AAG CTG TCG AAA        480
Tyr Gly Val Ser Thr Cys Asn Thr Thr Glu Gln Asp Lys Leu Ser Lys
145                 150                 155                 160

AAC GGC TCC TAC CCT TCC GGA CAC ACC TCT ATC GGC TGG GCG ACC GCC        528
Asn Gly Ser Tyr Pro Ser Gly His Thr Ser Ile Gly Trp Ala Thr Ala
        165                 170                 175

CTG GTG CTG GCC GAA ATC AAC CCG CAG CGC CAG AAT GAG ATT CTC AAG        576
Leu Val Leu Ala Glu Ile Asn Pro Gln Arg Gln Asn Glu Ile Leu Lys
        180                 185                 190

CGC GGC TAT GAG CTC GGT GAA AGT CGG GTG ATC TGC GGT TAC CAC TGG        624
Arg Gly Tyr Glu Leu Gly Glu Ser Arg Val Ile Cys Gly Tyr His Trp
        195                 200                 205

CAG AGC GAT GTT GAC GCC GCG CGG ATT GTC GGC TCG GCG GTG GTT GCA        672
Gln Ser Asp Val Asp Ala Ala Arg Ile Val Gly Ser Ala Val Val Ala
210                 215                 220

ACC CTG CAT ACC AAT CCG GCC TTC CAG CAG CAG CTG CAA AAA GCC AAA        720
Thr Leu His Thr Asn Pro Ala Phe Gln Gln Gln Leu Gln Lys Ala Lys
225                 230                 235                 240

GAC GAG TTT GCG AAA CAG CAG AAA TAG                                    747
Asp Glu Phe Ala Lys Gln Gln Lys
                245
```

(2) INFORMATION FOR SEQ ID NO:22:

(i) SEQUENCE CHARACTERISTICS:
        (A) LENGTH: 248 amino acids
        (B) TYPE: amino acid
        (D) TOPOLOGY: linear (ii) MOLECULE TYPE: protein (vi) ORIGINAL SOURCE:
        (A) ORGANISM: Klevsiella planticola
        (B) STRAIN: IFO 14939

(xi) SEQUENCE DESCRIPTION: SEQ ID NO:22:

```
Met Lys Lys Arg Val Leu Ala Leu Cys Leu Ala Ser Leu Phe Ser Val
1               5                   10                  15

Ser Ala Phe Ala Leu Val Pro Ala Gly Asn Asp Ala Thr Thr Lys Pro
                20                  25                  30

Asp Leu Tyr Tyr Leu Lys Asn Ala Gln Ala Ile Asp Ser Leu Ala Leu
            35                  40                  45

Leu Pro Pro Pro Pro Glu Val Gly Ser Ile Ala Phe Leu Asn Asp Gln
        50                  55                  60

Ala Met Tyr Glu Lys Gly Arg Leu Leu Arg Ala Thr Ala Arg Gly Lys
65                  70                  75                  80

Leu Ala Ala Glu Asp Ala Asn Leu Ser Ala Gly Val Ala Asn Ala
                85                  90                  95

Phe Ser Ala Ala Phe Gly Ser Pro Ile Ser Glu Lys Asp Ala Pro Ala
                100                 105                 110

Leu His Lys Leu Leu Thr Asn Met Ile Glu Asp Ala Gly Asp Leu Ala
            115                 120                 125

Thr Arg Gly Ala Lys Glu Lys Tyr Met Arg Ile Arg Pro Phe Ala Phe
130                 135                 140
```

```
Tyr Gly Val Ser Thr Cys Asn Thr Thr Glu Gln Asp Lys Leu Ser Lys
145                 150                 155                 160

Asn Gly Ser Tyr Pro Ser Gly His Thr Ser Ile Gly Trp Ala Thr Ala
            165                 170                 175

Leu Val Leu Ala Glu Ile Asn Pro Gln Arg Gln Asn Glu Ile Leu Lys
                180                 185                 190

Arg Gly Tyr Glu Leu Gly Glu Ser Arg Val Ile Cys Gly Tyr His Trp
            195                 200                 205

Gln Ser Asp Val Asp Ala Ala Arg Ile Val Gly Ser Ala Val Val Ala
        210                 215                 220

Thr Leu His Thr Asn Pro Ala Phe Gln Gln Gln Leu Gln Lys Ala Lys
225                 230                 235                 240

Asp Glu Phe Ala Lys Gln Gln Lys
                245
```

(2) INFORMATION FOR SEQ ID NO:23:

(i) SEQUENCE CHARACTERISTICS:
        (A) LENGTH: 735 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Serratia ficaria
        (B) STRAIN: IAM 13540

(ix) FEATURE:
        (A) NAME/KEY: CDS
        (B) LOCATION: 1..732

(xi) SEQUENCE DESCRIPTION: SEQ ID NO:23:

```
ATG AAA AAA ATA TTA TTA GCC ACA TTA AGC TGC GCC GCG TTG ACG CAG      48
Met Lys Lys Ile Leu Leu Ala Thr Leu Ser Cys Ala Ala Leu Thr Gln
1               5                   10                  15

TTT TCC TTT GCC GCC AAA GAT GTC ACT ACC CAC CCT GAG GTT TAT TTT     96
Phe Ser Phe Ala Ala Lys Asp Val Thr Thr His Pro Glu Val Tyr Phe
                20                  25                  30

CTG CAA GAA TCA CAG TCC ATC GAC AGC CTG GCA CTA TTG CCG CCG CCG    144
Leu Gln Glu Ser Gln Ser Ile Asp Ser Leu Ala Leu Leu Pro Pro Pro
            35                  40                  45

CCG GCG ATG GAC AGC ATT GAT TTC CTG AAT GAC AAA GCG CAA TAC GAC    192
Pro Ala Met Asp Ser Ile Asp Phe Leu Asn Asp Lys Ala Gln Tyr Asp
50                  55                  60

GCC GGG AAA ATA GTG CGC AAT ACT CCG CGT GGC AAG CAG GCT TAT GAT    240
Ala Gly Lys Ile Val Arg Asn Thr Pro Arg Gly Lys Gln Ala Tyr Asp
65                  70                  75                  80

GAC GCC CAC GTT GCC GGG GAC GGC GTT GCC GCC GCA TTT TCC AAC GCC    288
Asp Ala His Val Ala Gly Asp Gly Val Ala Ala Ala Phe Ser Asn Ala
                85                  90                  95

TTC GGC CTA GAA ATA GCC CAA CGG AAA ACG CCG GAG CTG TTT AAG CTG    336
Phe Gly Leu Glu Ile Ala Gln Arg Lys Thr Pro Glu Leu Phe Lys Leu
            100                 105                 110

GTG ATG AAA ATG CGT GAA GAC GCC GGC GAT TTG GCG ACC CGC AGC GCC    384
Val Met Lys Met Arg Glu Asp Ala Gly Asp Leu Ala Thr Arg Ser Ala
        115                 120                 125

AAA AAT CAC TAT ATG CGC ATT CGC CCC TTT GCG TTT TAT AAC GAA GCG    432
Lys Asn His Tyr Met Arg Ile Arg Pro Phe Ala Phe Tyr Asn Glu Ala
```

| | | |
|---|---|---|
| 130 | 135 | 140 |

```
ACC TGC CGA CCG GAC GAA GAA AGC ACC CTG TCG AAG AAC GGT TCT TAC    480
Thr Cys Arg Pro Asp Glu Glu Ser Thr Leu Ser Lys Asn Gly Ser Tyr
145                 150                 155                 160

CCT TCC GGC CAT ACC ACC ATC GGC TGG GCG ACC GCG CTG GTG CTG GCT    528
Pro Ser Gly His Thr Thr Ile Gly Trp Ala Thr Ala Leu Val Leu Ala
                165                 170                 175

GAA ATC AAC CCC GCC AGG CAG GGT GAA ATC CTG CAG CGC GGC TAT GAT    576
Glu Ile Asn Pro Ala Arg Gln Gly Glu Ile Leu Gln Arg Gly Tyr Asp
            180                 185                 190

ATG GGC CAA AGC CGG GTT ATC TGC GGT TAT CAC TGG CAA AGC GAC GTG    624
Met Gly Gln Ser Arg Val Ile Cys Gly Tyr His Trp Gln Ser Asp Val
        195                 200                 205

ACT GCG GCG CGC ATG GCG GCG TCG GCC ATG GTG GCG CGT TTG CAT GCC    672
Thr Ala Ala Arg Met Ala Ala Ser Ala Met Val Ala Arg Leu His Ala
    210                 215                 220

GAA CCC ACC TTC GCC GCC CAG CTG CAA AAG GCC AAA GAC GAA TTC AAC    720
Glu Pro Thr Phe Ala Ala Gln Leu Gln Lys Ala Lys Asp Glu Phe Asn
225                 230                 235                 240

GGC CTG AAA AAG TAA                                                735
Gly Leu Lys Lys
```

(2) INFORMATION FOR SEQ ID NO:24:

(i) SEQUENCE CHARACTERISTICS:
        (A) LENGTH: 244 amino acids
        (B) TYPE: amino acid
        (D) TOPOLOGY: linear (ii) MOLECULE TYPE: protein (vi) ORIGINAL SOURCE:
        (A) ORGANISM: Serratia ficaria
        (B) STRAIN: IAM 13540

(xi) SEQUENCE DESCRIPTION: SEQ ID NO:24:

```
Met Lys Lys Ile Leu Leu Ala Thr Leu Ser Cys Ala Ala Leu Thr Gln
 1               5                  10                  15

Phe Ser Phe Ala Ala Lys Asp Val Thr Thr His Pro Glu Val Tyr Phe
                20                  25                  30

Leu Gln Glu Ser Gln Ser Ile Asp Ser Leu Ala Leu Leu Pro Pro Pro
            35                  40                  45

Pro Ala Met Asp Ser Ile Asp Phe Leu Asn Asp Lys Ala Gln Tyr Asp
        50                  55                  60

Ala Gly Lys Ile Val Arg Asn Thr Pro Arg Gly Lys Gln Ala Tyr Asp
65                  70                  75                  80

Asp Ala His Val Ala Gly Asp Gly Val Ala Ala Phe Ser Asn Ala
                85                  90                  95

Phe Gly Leu Glu Ile Ala Gln Arg Lys Thr Pro Glu Leu Phe Lys Leu
                100                 105                 110

Val Met Lys Met Arg Glu Asp Ala Gly Asp Leu Ala Thr Arg Ser Ala
            115                 120                 125

Lys Asn His Tyr Met Arg Ile Arg Pro Phe Ala Phe Tyr Asn Glu Ala
        130                 135                 140

Thr Cys Arg Pro Asp Glu Glu Ser Thr Leu Ser Lys Asn Gly Ser Tyr
145                 150                 155                 160

Pro Ser Gly His Thr Thr Ile Gly Trp Ala Thr Ala Leu Val Leu Ala
                165                 170                 175

Glu Ile Asn Pro Ala Arg Gln Gly Glu Ile Leu Gln Arg Gly Tyr Asp
            180                 185                 190
```

```
Met Gly Gln Ser Arg Val Ile Cys Gly Tyr His Trp Gln Ser Asp Val
        195                 200                 205

Thr Ala Ala Arg Met Ala Ala Ser Ala Met Val Ala Arg Leu His Ala
        210                 215                 220

Glu Pro Thr Phe Ala Ala Gln Leu Gln Lys Ala Lys Asp Glu Phe Asn
225                 230                 235                 240

Gly Leu Lys Lys
```